(12) United States Patent
Abou El Kheir

(10) Patent No.: US 7,666,181 B2
(45) Date of Patent: Feb. 23, 2010

(54) MULTI-PURPOSE MINIMALLY INVASIVE INSTRUMENT THAT USES A MICRO ENTRY PORT

(76) Inventor: Tarek Ahmed Nabil Abou El Kheir, 3705 Braodway, Apt. 2R, Astoria, NY (US) 11103

( * ) Notice: Subject to any disclaimer, the term of this patent is extended or adjusted under 35 U.S.C. 154(b) by 0 days.

(21) Appl. No.: 12/185,082

(22) Filed: Aug. 2, 2008

(65) Prior Publication Data

US 2008/0287926 A1 Nov. 20, 2008

(51) Int. Cl.
*A61B 17/00* (2006.01)
(52) U.S. Cl. .............................. 606/1; 606/130; 600/104
(58) Field of Classification Search ...................... 606/1, 606/118–120, 130, 138–140, 160, 167, 170; 600/101–104, 108, 109
See application file for complete search history.

(56) References Cited

U.S. PATENT DOCUMENTS

| | | | | |
|---|---|---|---|---|
| 3,964,468 | A | * | 6/1976 | Schulz ........................ 600/564 |
| 5,133,735 | A | * | 7/1992 | Slater et al. .................. 606/205 |
| 5,336,238 | A | * | 8/1994 | Holmes et al. .............. 606/208 |
| 5,389,077 | A | | 2/1995 | Melinyshyn |
| 5,441,059 | A | * | 8/1995 | Dannan ....................... 128/898 |
| 5,527,339 | A | * | 6/1996 | Koscher et al. ............. 606/205 |
| 5,718,714 | A | | 2/1998 | Livneh |
| 5,865,817 | A | | 2/1999 | Moenning |
| 5,925,064 | A | | 7/1999 | Meyers |
| 6,565,554 | B1 | | 5/2003 | Niemeyer |
| 6,974,449 | B2 | | 12/2005 | Niemeyer |
| 7,160,309 | B2 | | 1/2007 | Voss |
| 7,297,142 | B2 | | 11/2007 | Brock |
| 2006/0122580 | A1 | | 6/2006 | Dannan |
| 2006/0287641 | A1 | | 12/2006 | Perlin |
| 2006/0287643 | A1 | | 12/2006 | Perlin |
| 2008/0177265 | A1 | | 7/2008 | Le Chot |

FOREIGN PATENT DOCUMENTS

| | | |
|---|---|---|
| WO | WO/2006/005061 | 1/2006 |
| WO | WO/2006/039279 | 4/2006 |
| WO | WO/2008/042134 | 4/2008 |

\* cited by examiner

*Primary Examiner*—Ahmed M Farah
(74) *Attorney, Agent, or Firm*—Dorothy S. Morse

(57) ABSTRACT

A multi-purpose minimally invasive instrument having a small diameter elongated rod with a distal end that receives different interchangeable tools for a variety of uses, and also a handle used by an operator to control the interchangeable tool by manipulating the electricity it receives from a generator. The rod enters a cavity through a very small diameter telescopic port, which provides it with added support during its use. Interchangeable tools comprising imaging/surgical/sensing/electromagnet/radiofrequency/laser/heat-generating probes and/or other devices enter the cavity, supported by an introducer removed after tool attachment, one-at-a-time through a regular-size port that is concurrently used by an endoscope/camera. The instrument is adaptable for therapeutic, investigative, and/or other applications, in any space. An important medical benefit is the usage of many tools simultaneously while employing only one regular-size port and a very small diameter port for each additional tool used, which expedites patient recovery with excellent cosmetic outcome.

20 Claims, 11 Drawing Sheets

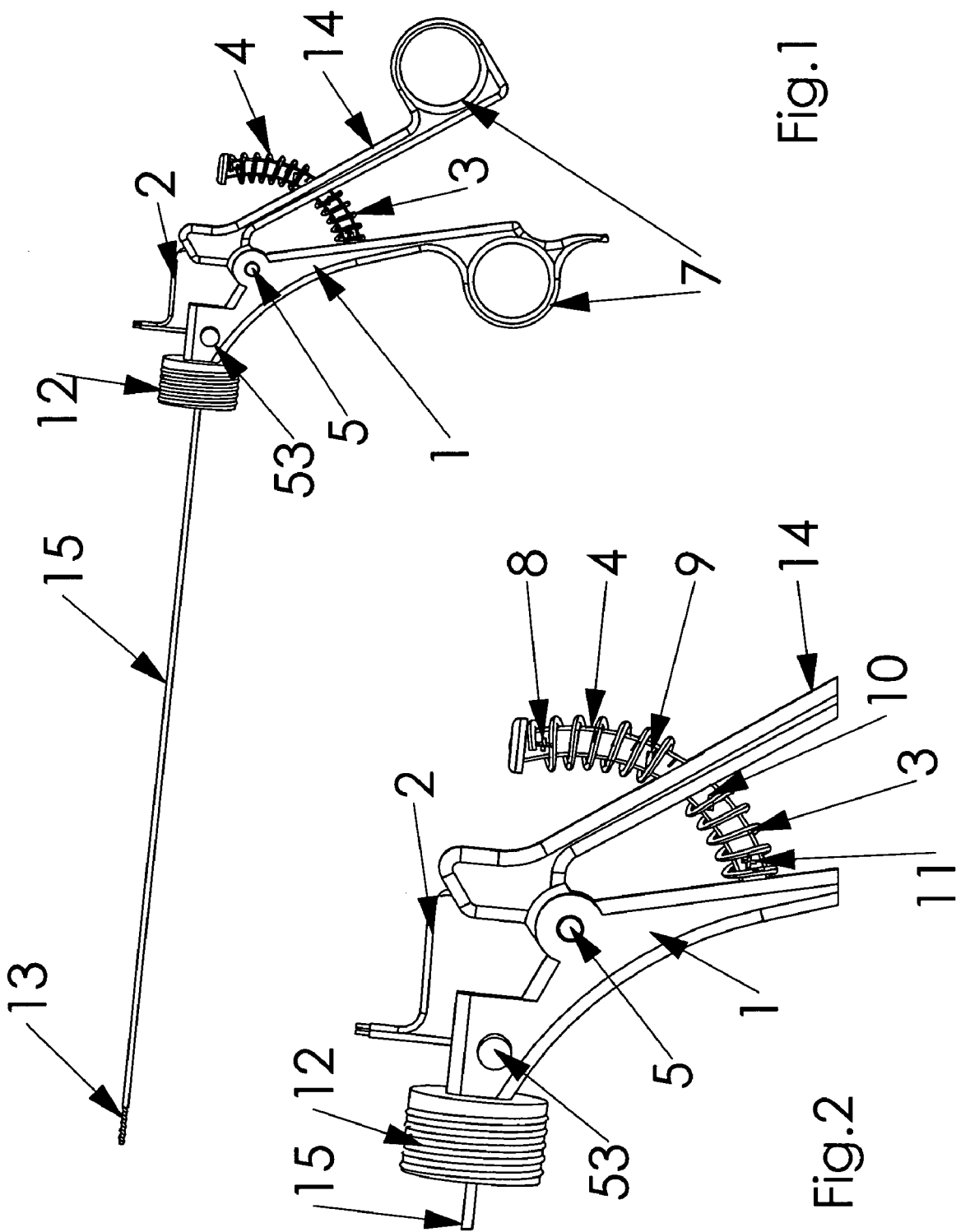

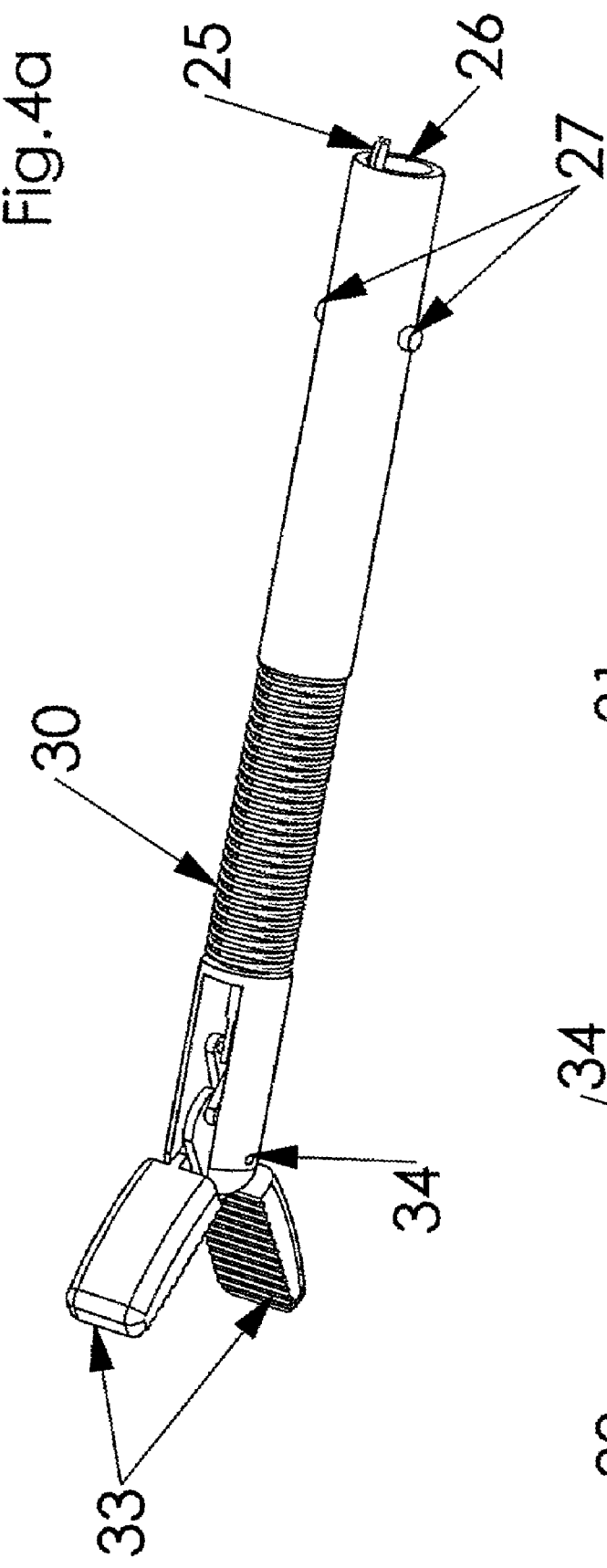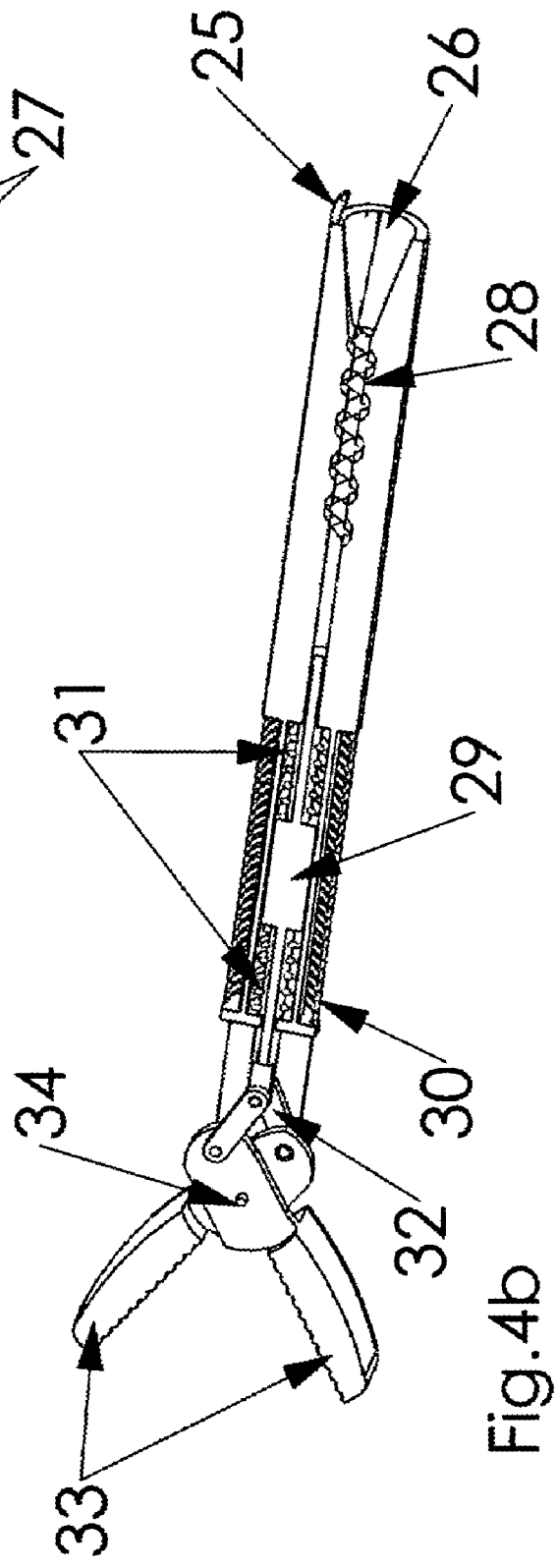

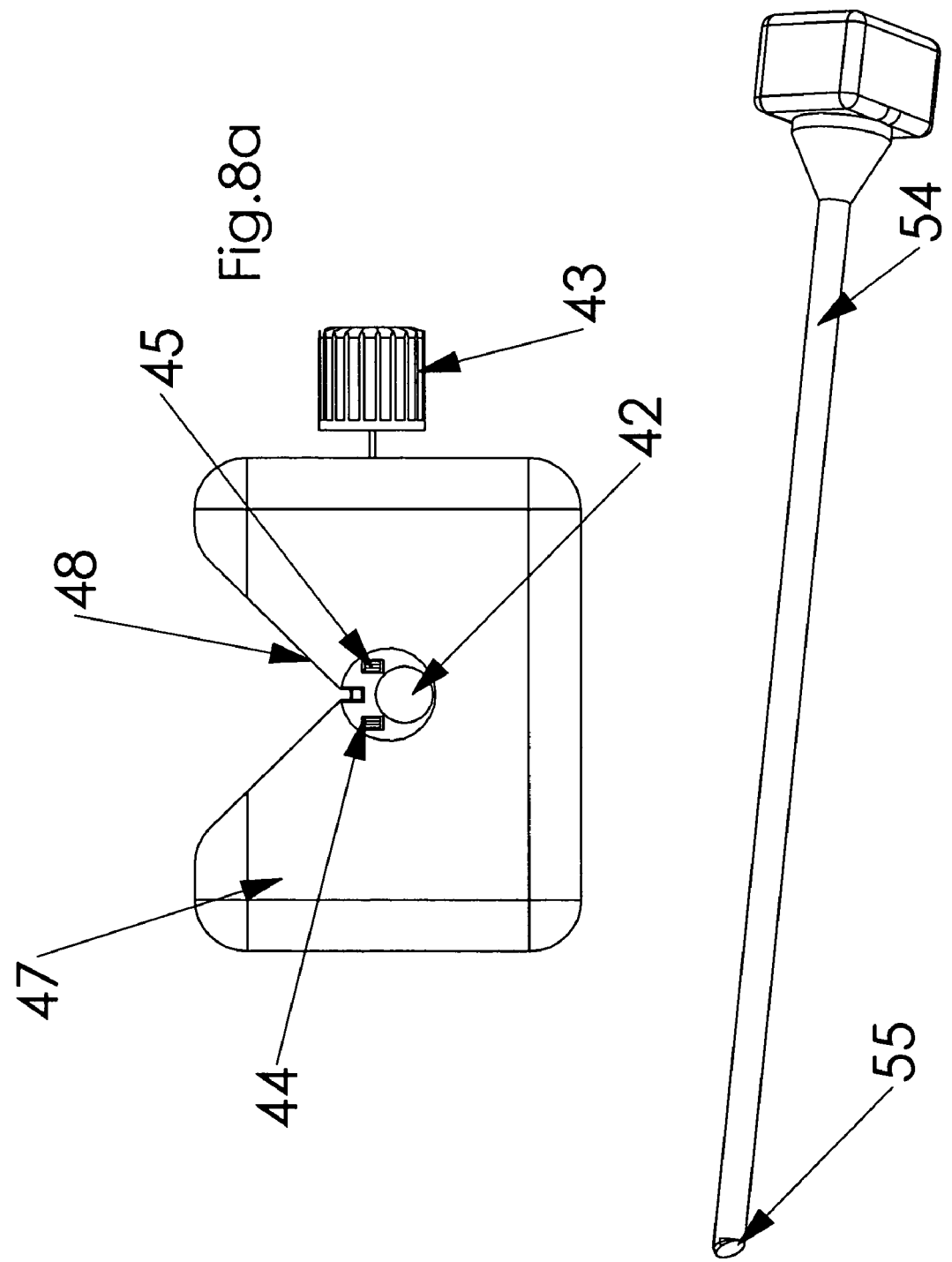

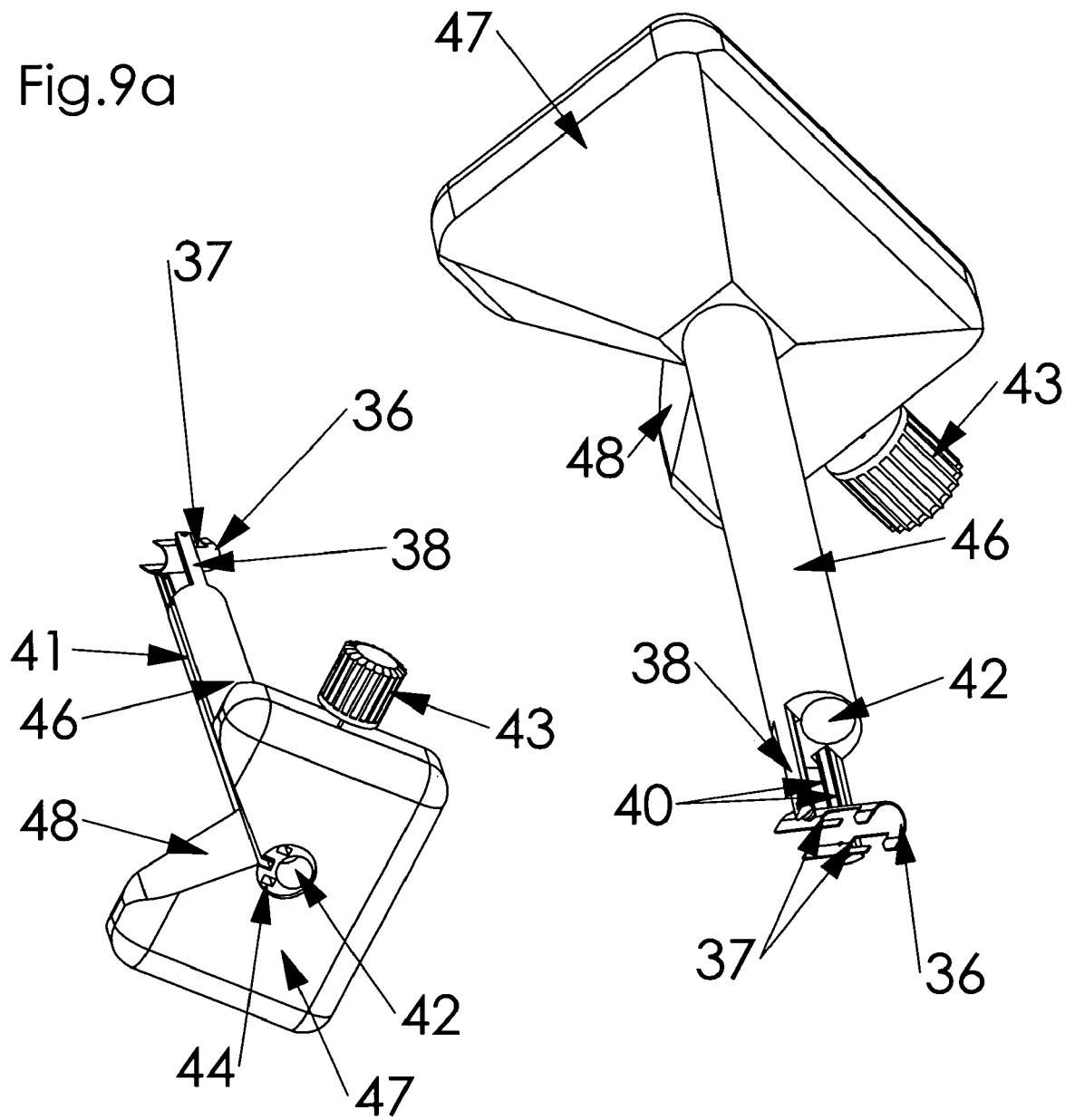

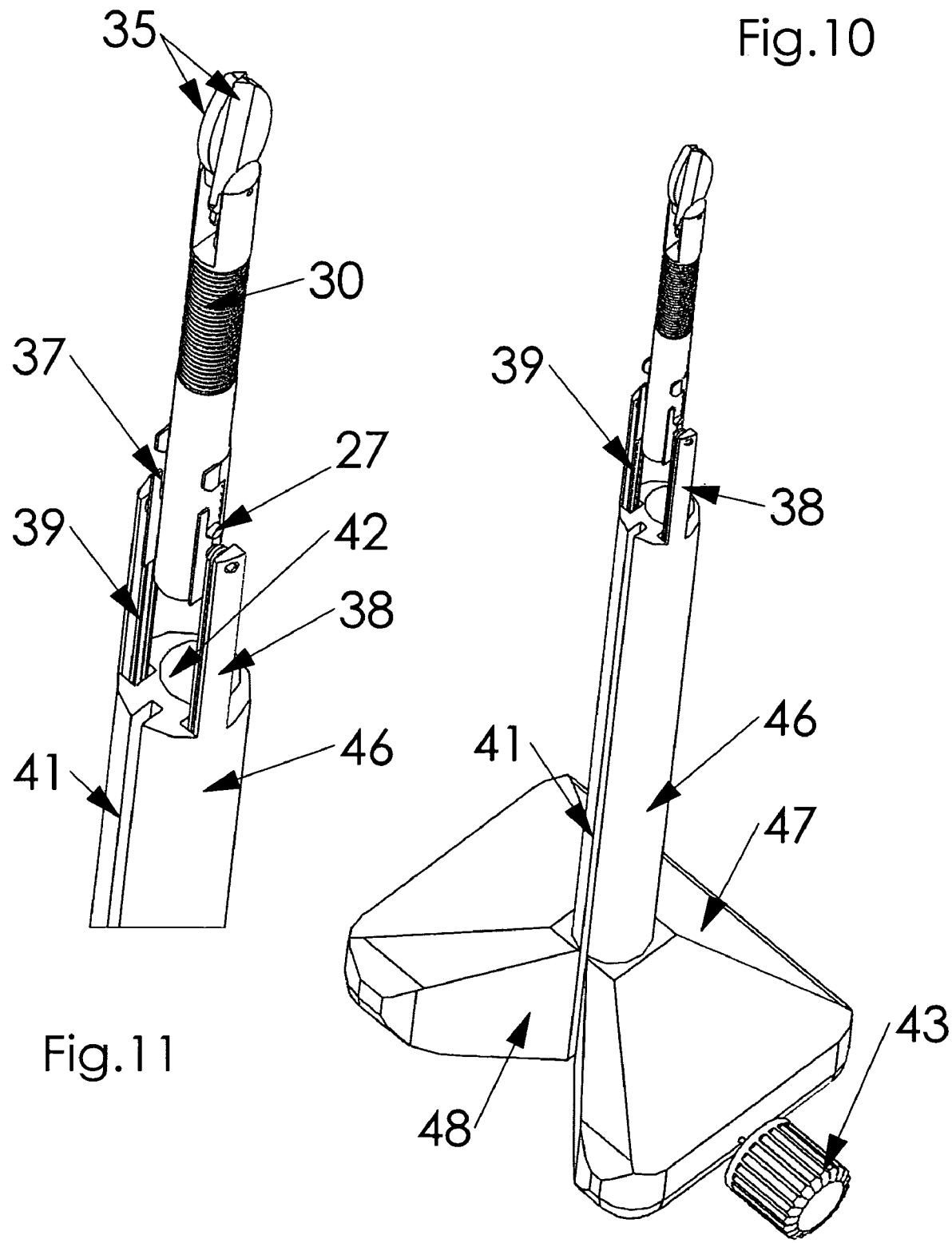

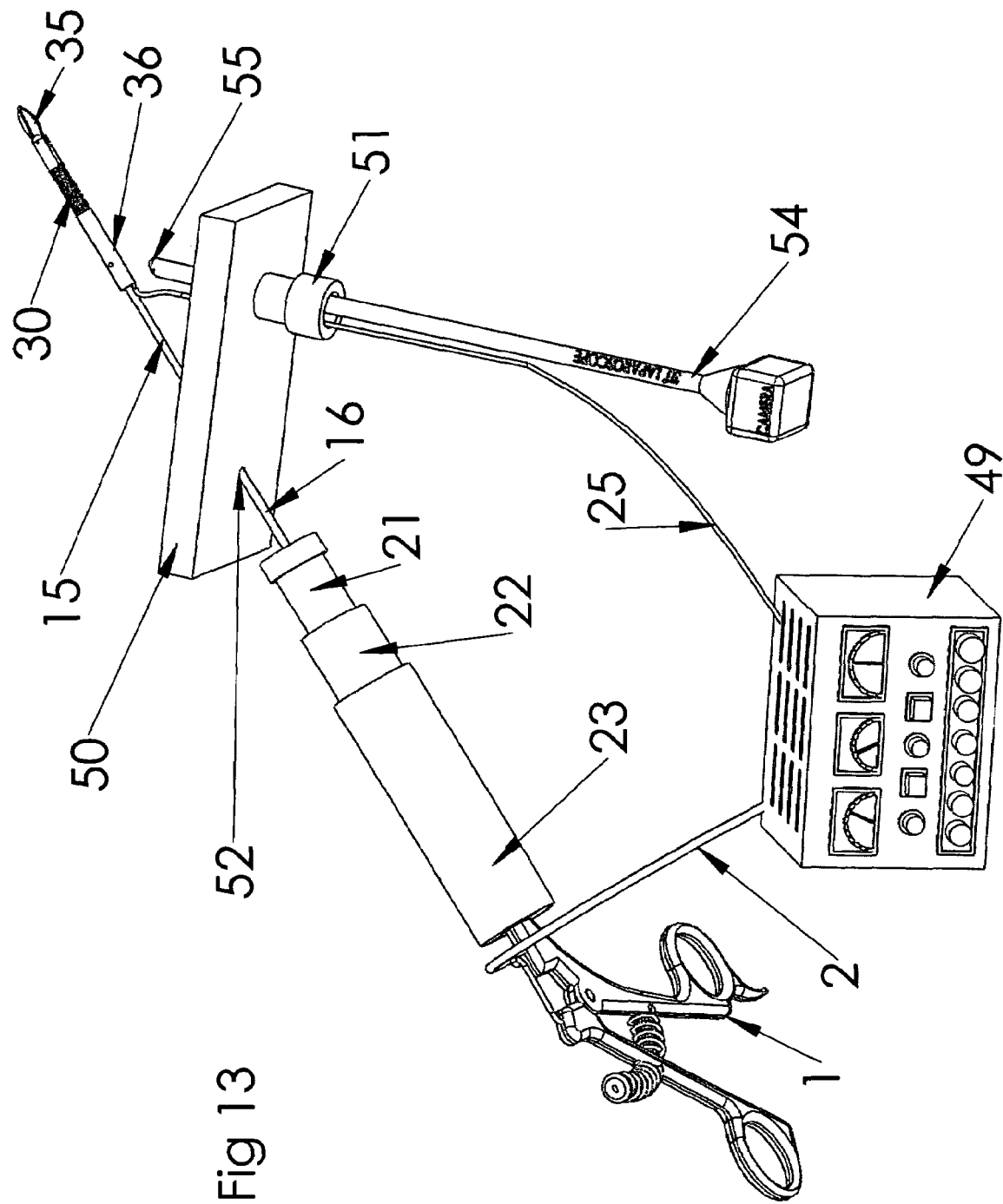

MULTI-PURPOSE MINIMALLY INVASIVE INSTRUMENT THAT USES A MICRO ENTRY PORT

CROSS-REFERENCES TO RELATED APPLICATION

None

BACKGROUND

1. Field of the Invention

This invention relates to the field of hand-manipulated instruments used for surgical, therapeutic, investigative, and other medical or non-medical applications in any space, specifically to a multi-purpose and minimally invasive instrument having a small diameter elongated rod with a distal end that receives different interchangeable tools one-at-a-time for a variety of uses. An operator uses the scissors-like handle of the instrument, with its fixed arm and its movable arm, to control the tool secured to the distal end of its elongated rod by manipulating the amount and/or polarity of electricity produced by a generator electrically connected between the movable arm and the tool (or other electrically connected device capable of transmitting metered amounts of electricity to the tool). The movable arm is initially placed into a neutral position, wherein operator manipulation of the movable arm can occur in two directions, toward the fixed arm to increase the amount of electricity transmitted to the tool and enhance a first operative effect/function, with operator manipulation of the movable arm away from the fixed arm also increasing the amount of electricity transmitted to the tool, perhaps with opposite polarity, to enhance a different operative effect/function (for example a first operative effect/function might be to close the blades of endoscopic scissors, with the second effect/function being to open the blades of the same endoscopic scissors). Thus, for a tool that opens and closes, operator manipulation of the movable arm away from the fixed arm could be used to open the jaws of the tool, while operator manipulation of the movable arm toward the fixed arm could close the jaws of the same tool. For tools that do not have an opening or closing action, operator manipulation of the movable arm in one direction could cause a first type of therapeutic or investigative effect/function, with operator manipulation of the movable arm in the opposite direction causing a second type of therapeutic or investigative effect/function, such as the alternate execution of cutting and coagulation actions by the same laser probe. It is also contemplated for the amount of movement of the movable arm in either direction away from its initial centrally-located neutral position to correlate to the amount of therapeutic or investigative effect/function achieved. Thus, springs are preferably used to create a biasing effect that permits an operator to sense an increase in resistance as operator-regulated force is increasingly applied, to naturally mimic the resistance that would otherwise be felt during direct manual manipulation of tissue by the tool's operative tip. The biasing springs also make the operator use more force to get the movable arm closer to a position of near maximum displacement (indicated by a plus sign in the accompanying illustrations), which results in the creation of more closure force between the blades at the tip of the interchangeable tool and less closure force between the blades when the operator brings the movable arm back toward its neutral starting position. Stored energy in the biasing spring further assists the operator in bringing the movable arm back to its neutral starting position as the operator-applied force decreases. Thus, when needed for use in a limited-access cavity, the elongated rod of the present invention enters the cavity through a very small diameter telescopic port, which provides the small diameter elongated rod with added support during its use. Interchangeable tools needed for use in the cavity include, but are not limited to, imaging probes, surgical probes, sensor probes, clamping devices, cutting instruments, electromagnets, radio frequency probes, laser probes, laser cutting devices, laser coagulating instruments, heat-generating probes, image sensing probes, ultrasound probes, magnetic resonance imaging probes, and a variety of other devices. Such tools enter the cavity independently from the instrument through a regular-size port opening while being temporarily secured to the pivoting cradle of a tool introducer that is later removed from the regular-size port opening once the tool becomes attached to the distal end of the elongated rod. In its place when the tool introducer is withdrawn, a sheath with a central opening may be inserted through the regular-size port opening to separate the wires or cables extending to different tools present within the cavity and thereby prevent the wires and cables from becoming entangled during tool use. Exit of the tool from the cavity is also accomplished via the cradle of the tool introducer. A bore longitudinally through the tool introducer permits concurrent use of an endoscope/camera in the same regular-size port opening employed by the tool introducer, and thereby precludes the need for an additional patient incision to insert a camera and lighting needed for operator viewing of targeted tissue and assistance in the mounting of a tool on the distal end of the elongated rod. While the same tool introducer can be used to exchange the tools on the same present invention instrument, a single tool introducer can be used to mount, exchange, and/or remove the tools from all of the present invention instruments simultaneously or sequentially used within a cavity to accomplish needed surgical, investigative, and therapeutic procedures. Once the tool introducer is removed, any small diameter electrical wiring or cable used to connect the mounted tool to a source of operative power remains extended through the regular-size port opening, which is also sufficiently large to receive the same or different optical system (endoscope/camera), as well as the small diameter electrical wiring or cable connected to the tools mounted on the elongated rods of any other present invention instruments positioned within the same cavity. As previously mentioned, a sheath can be inserted into the regular-size port opening after all of the tools needed in a cavity are present and the tool introducer is withdrawn, with the sheath being employed to maintain spaced-apart positioning between the optical system and electrical wiring or cables during tool use. Although it is contemplated for the wiring or cable for all present invention instruments used in one cavity to extend through one regular-size port opening, the elongated rod of each present invention instrument employed would individually enter the cavity through its own independent micro opening that is not much bigger than a needle mark and capable of healing with little or no visible scar. Further, as a result of the present invention using a very narrow diameter elongated rod to support a tool (instead of the tube used in prior art surgical, therapeutic, and investigative devices) and also as a result of the present invention having an external means of controlling tool operation that can be carried through the cavity wall via an independent (regular-size) port opening (in contrast to the internal tool control means (i.e. cable/wiring) carried within the tube of prior art surgical, therapeutic, and investigative devices), the present invention can use smaller diameter (micro port) openings (for example, in common intra-abdominal endoscopic surgeries, micro openings with present invention use can be approximately two millimeters in diameter or less)

than is possible for prior art devices performing similar functions, with the smaller micro openings being able to heal faster and with little or no visible scar, for improved patient satisfaction. Thus, in summary, an important surgical benefit of the present invention is the potential use of several surgical, investigative, and/or therapeutic tools simultaneously in a cavity with only one very small diameter and fast-healing micro port opening made in the cavity's wall for each minimally-invasive instrument employed, with all of the tools, electrical wiring and cables needed for tool operation, as well as an optical system (endoscope/camera), having their introduction into the cavity (and removal therefrom) being accomplished via a tool introducer with a pivoting cradle that is inserted through a single regular-size port opening, which expedites patient recovery with excellent cosmetic outcome.

2. Description of the Related Art

Although surgical and other medical procedures have undergone much advancement over the years to simplify them, reduce their duration of use, require less manpower, improve cosmetic outcome, and/or lessen the time needed for patient recovery, there still is opportunity for improvement in all of these areas when the procedure requires entry through a cavity wall, particularly relating to reduced patient recovery time and a good cosmetic result. Thus, instead of making one or more lengthy incisions at the beginning of a surgical or other medical procedure to create one large access opening near to the organ or tissue needing surgical assistance, for many surgical procedures it is now common to employ several smaller openings through the skin (each between approximately five and twelve millimeters in diameter), with each such smaller opening configured for the insertion of an instrument that one or more surgeons can use alone or in concert with at least one other instrument (that extends into the cavity through a separate and independent opening) to perform specific investigative and/or therapeutic operations. Even though the use of small openings reduces the risk of infection and produces a cosmetic result better than that achieved by the previous practice of making one or more lengthy surgical incisions, prior art devices still use tubes (instead of rods) to mount the needed probes or therapeutic devices for entry into a cavity, wherein at least a part of the operative controls for mounted devices are carried within the tube, thus limiting the minimum size of the port opening that can be used for entry through a cavity wall (especially large cavities like the intra-abdominal cavity) to approximately five millimeters. Small tubes are also more likely to bend or break than a rod because of their hollow structure, another limiting factor of tube use. While a five millimeter opening in a patient's skin will produce significantly less scar tissue than the lengthy incisions previously used, a five millimeter opening is still sufficiently large to pose an infection risk, and once healed it still remains a visible reminder of the surgery. In contrast, the present invention introduces an elongated rod into a cavity through a much smaller diameter opening (a micro opening typically having a diameter dimension of approximately two millimeters or less), which is similar in size to the opening produced by the tip of a needle and can often heal without any visible scar. Tool control for multiple present invention instruments is accomplished through a single regular-size port opening that is concurrently used by an optical system (endoscope/camera), which is needed to provide operator viewing inside the cavity. Thus, via the use of one or more present invention instruments simultaneously or in sequence to conduct a medical or surgical procedure, there is only one incision mainly at risk for infection and formation of scar tissue, which is the regular-size port opening made for tool and optical system introduction (as the other port openings used are no greater than needle marks that typically heal without scars), thus the cosmetic outcome for a patient is improved and recovery time is also reduced.

The invention thought to be the closest to the present invention is the invention found in U.S. Pat. No. 5,441,059 to Dannan (1995). Although both the Dannan invention and the present invention provide methods of minimally invasive surgery using a larger primary incision for inserting surgical heads/tools and at least one smaller secondary incision for insertion of a receiving end of a handle used by the operator to control an attached surgical head/tool, the present invention has many advantages over the Dannan invention. One important advantage is the present invention's use of a rod as the tool-receiving end of the operator's hand grip, instead of a tubular structure through which power can be sent to the surgical head/tool for its actuation, as in the Dannan invention (column 5, lines 21-28). A rod is less likely to bend or break than a tubular structure, and permits a smaller diameter incision in a patient. As a result, instead of requiring a secondary incision of approximately 2.8 to 3.2 mm (as in the Dannan invention column 4, lines 31-34), the present invention rod can be successfully used with a secondary incision of only 2 mm. Every reduction in incision size is significant and means less infection risk, faster patient recovery, and less scarring. Other important differences between the present invention and the Dannan invention include the present invention's use of a telescoping port assembly for protection and support of its tool-supporting rod (it also allows for rotational movement), a tool introducer inserted through the larger primary incision that has a pivoting cradle and a control knob positioned outside the cavity for operator control of cradle movement to provide facilitated attachment of a tool to the distal tip of its tool-supporting rod, a longitudinally-extending interior laparoscopic bore through the tool introducer that ensures adequate operator viewing of all work performed within a cavity for enhanced safety, an exterior channel on the tool introducer adapted for temporarily containing and protecting electrical wiring or cables attached to a tool during insertion of the cradle through a regular-size port opening in a cavity wall, a beveled outer surface on the tool introducer configured for facilitated release of the electrical wiring and cables from its exterior channel, and a sheath that is usable after all of the tools needed in a cavity are present and the tool introducer has been withdrawn, with the sheath having a central opening configured for insertion of an optical system (endoscope/camera) and a plurality of exterior channels each configured for supporting the wiring/cables attached to one of the inserted tools to maintain the wiring/cables from different tools separate from one another and prevent them from becoming entangled as a result of tool use. At a minimum, the lack of a control knob for selective tilting of the tool introducer cradle for tool attachment from a location outside the cavity, the lack of a longitudinally-extending interior laparoscopic bore through the tool introducer designed to allow the concurrent introduction of an optical system (endoscope/camera) with it through the same cavity port to ensure adequate operator viewing of all work performed within a cavity for enhanced safety, and lack of a supportive entry port means to protect and strengthen the small rod used for tool attachment especially in its lateral movement (side to side movement) in which the rod experiences the highest level of stress to its material (which allows the use of a smaller rod diameter), are significant omissions from the Dannan invention that make it less desirable for use than the present invention. All of the above-mentioned features of the present invention not provided in the Dannan invention, are important as they contribute to the enhanced ease, convenience, safety, and/or expediency of present invention use.

Another distinguishing difference between the present invention and the Dannan invention is the handle grip of the present invention through which the operator can control the action of surgical tools connected to the distal end of an attached rod, wherein first and second biasing springs help to provide metered power to each surgical tool for its control when mounted on the rod's distal end, with the electricity that is manipulated by the handle grip being produced by a generator electrically connected between the movable arm and the mounted tool. The biasing springs also allow an operator to sense an increase in resistance with an increase in operator-applied force that mimics the resistance the operator would otherwise feel during direct manipulation of tissue by the interchangeable tool's operative tip. Such resistance sensing is important to an operator and not provided by the Dannan invention. The present invention also has an arcuate projection of rigid construction positioned between its fixed and movable arms. The arcuate projection acts as a deployment guide for one of its biasing springs, and a portion of the arcuate projection/guide passes through the movable arm of the present invention when an operator applies a force that places the movable arm out of its neutral starting position and causes it to move father away from its fixed arm, or closer to it. This arcuate projection works as an electric current control resistor, where the resistance is at its highest when the movable arm is in the central neutral position. Lack of the arcuate projection in the Dannan invention, in addition to the many other features of the present invention identified above that are not found in the Dannan invention disclosure, distinguish the present invention from Dannan. As a result, no other invention is currently known to have the same structure, or all of the features and benefits provided by the present invention.

BRIEF SUMMARY OF THE INVENTION

The primary object of this invention is to provide a multi-purpose and minimally invasive hand-manipulated instrument for use in surgical, therapeutic, investigative, and other medical or non-medical applications in any space, that in surgical applications can use a very small micro port opening in a patient, much smaller than the size of openings currently employed with prior art instruments working within an abdominal or other body cavity, wherein the very small micro opening used reduces patient recovery time and improves cosmetic outcome. Another object of this invention is to provide a multi-purpose and minimally invasive hand-manipulated instrument for use in surgical, therapeutic, investigative, and other medical or non-medical applications in any space that allows the operator of a tool mounted on the instrument's elongated rod to sense an increase in resistance correlating to the increase in operator-applied force that mimics the resistance that the operator would otherwise feel during direct manipulation of tissue and other matter/substances using the tool's operative tip. A further object of this invention is to provide a multi-purpose and minimally invasive hand-manipulated instrument for use in surgical, therapeutic, investigative, and other medical or non-medical applications in any space that can be adapted for different applications in the same or different space via the use of readily interchangeable tools. It is also an object of this invention to provide a multi-purpose and minimally invasive hand-manipulated instrument for use in non-medical search/rescue and scientific research applications, in addition to a variety of surgical, therapeutic, and investigative medical applications. A further object of this invention is to provide a multi-purpose and minimally invasive hand-manipulated instrument for use in surgical, therapeutic, investigative, and other medical or non-medical applications in any space wherein tool mounting, exchange, and/or removal from the instrument's elongated rod takes place via use of a tool introducer that is inserted into the cavity through a separate (regular-size, not micro) port opening, the same opening already required to provide an optical system for operator viewing within the cavity, thereby eliminating the need for separate incisions in a patient for tool introduction and operator viewing equipment. It is a further object of this invention to provide a multi-purpose and minimally invasive hand-manipulated instrument for use in surgical, therapeutic, investigative, and other medical or non-medical applications in any space wherein multiple present invention instruments can be used simultaneously in a cavity to conduct various procedures, with each instrument being inserted through a separate very small micro opening in the cavity wall, and further with the wiring or cable that provide needed power to the tools on all of the present invention instruments being brought into the cavity through a single regular-size port opening that is also used for bringing an optical system (endoscope/camera) into the cavity. It is also an object of this invention to provide a multi-purpose and minimally invasive hand-manipulated instrument for use in surgical, therapeutic, investigative, and other medical or non-medical applications in any space that is durably constructed and sufficiently strong for intended applications. Another object of this invention is to provide a multi-purpose and minimally invasive hand-manipulated instrument for use in surgical, therapeutic, investigative, and other medical or non-medical applications in any space that is durably constructed and made from materials able to withstand without premature deterioration the repeated sanitizing procedures required for body cavity insertions.

The present invention when properly made and used provides an instrument with a small diameter elongated rod having a distal end that receives different interchangeable tools one-at-a-time for a variety of uses, including but not limited to surgical uses in abdominal and other body cavities, although non-medical applications involving search/rescue and scientific research are equally contemplated. Interchangeable tools used with the present invention instrument can include, but are not limited to, imaging probes, surgical probes, sensor probes, clamping devices, cutting instruments, electromagnets, radio frequency probes, laser probes, laser cutting devices, laser coagulating instruments, heat-generating probes, image sensing probes, ultrasound probes, and magnetic resonance imaging probes. In surgical applications, the small diameter elongated rod enters and leaves a cavity through a very small diameter port (positioned within a micro opening having a diameter dimension of approximately two millimeters or less that is able to heal rapidly with little or no visible scar), while tools enter and leave the cavity independently from the elongated rod through a larger diameter (regular-size) port opening, which is approximately five millimeters or more in diameter dimension and can also be used for insertion of an optical system (endoscope/camera) into the cavity. The optical system can be inserted into a cavity through a longitudinally-extending bore in the tool introducer, as well as after the tool introducer has been removed from the regular-size port opening, and when all of the tools needed in a cavity are present, a sheath can be used in the regular-size port opening with optical system and electrical wiring or cables to maintain spaced-apart positioning for them and keep them from becoming entangled during tool use. Thus, with present invention use, only one regular-size port opening (which typically leaves a small scar after closure) needs to be made in a patient, and all tools employed in the cavity (other than the optical system needed for operator viewing) are each mounted on the elongated rod of a different present invention instrument that passes independently through the cavity wall via a separate micro opening, which is small enough that it has an excellent chance for rapid healing with little or no visible scar (in a manner similar to the fast healing typically experienced with needle marks made through the skin). Thus, patient recovery time is reduced, cosmetic outcome is improved, and patient satisfaction is also typically enhanced. It is contemplated for the tool introducer to have a pivoting cradle that temporarily and securely supports each tool needed in the cavity as it passes through the cavity wall, and once inside the cavity the tool introducer would also be used to assist in mounting the tool upon the distal end of the elongated rod. A control knob outside the cavity and associated with the tool introducer can be used to pivot the cradle to facilitate tool mounting, as needed. The tool introducer is removed from the regular-size port opening after the tool it carried into the cavity becomes attached to the elongated rod. The tool introducer can be reinserted through the regular-size port opening in the cavity wall as many times as are needed, without additional trauma to a patient, to mount tools on the elongated rod of each present invention instrument to be used in the cavity simultaneously or in sequence, or to exchange one tool for another on the elongated rod of the same present invention instrument. After all tools needed in a cavity are present, a sheath can be inserted through the regular-size port opening to maintain spaced-apart positioning for the optical system and electrical wiring or cables attached to the tools, to prevent them from becoming entangled during tool use. By inserting the elongated rod and tools through separate openings, only one of those openings needs to be a larger regular-size port opening, and all other surgical openings in the patient can be very small micro openings that heal rapidly with little or no visible scar. Use of a very small diameter elongated rod in the present invention, instead of a tube that internally carries operative control means for a mounted tool, necessitates the use of external tool control means. Thus, the movable arm of each present invention instrument is connected to a generator or other source of operative power for the tool mounted on its elongated rod, with the power source being electrically connected to the mounted tool via wiring or cable that extends through the regular-size port opening. When the elongated rods of multiple present invention instruments are inserted into the same cavity, it is contemplated for all of the wiring or cables connected to the multiple mounted tools to extend through the same regular-size port opening, and remain there until the tool is withdrawn from the cavity upon the cradle of the tool introducer (with or without a sheath to prevent their entanglement). It is also contemplated for the regular-size port opening to be sufficiently large for an optical system (endoscope/camera) to be inserted through it simultaneously with the electrical wiring and/or cables needed for tool operation. To allow concurrent use of an optical system (endoscope/camera) and a tool introducer through a single regular-size port opening when the tool introducer is being used to mount or exchange a tool on an elongated rod (and eliminate the need for an independent patient incision for the optical system), the tool introduced preferably contains a longitudinally-extending bore of sufficient size for stable support of the optical system (endoscope/camera). Thus, the bore is available for insertion of an endoscope/camera any time before or after the tool introducer is positioned within the regular-size port opening. Thus, no activity within a cavity needs to be performed blindly, resulting in improved safety in medical applications. An operator uses a scissors-like handle on the present invention instrument, with its fixed arm and its movable arm, to control the tool mounted on the distal end of its elongated rod by manipulating the amount of electricity produced by a generator electrically connected between the movable arm and the mounted tool (or other power source capable of transmitting metered amounts of electricity to the tool). The movable arm is initially placed into a neutral position, wherein operator manipulation of the movable arm can occur in two directions, toward the fixed arm to increase the amount of electricity transmitted to the tool and enhance a first operative effect/function, with operator manipulation of the movable arm away from the fixed arm also increasing the amount of electricity transmitted to the tool but enhancing a different operative effect/function, perhaps with opposite polarity. Thus, for a tool that opens and closes, operator manipulation of the movable arm toward the fixed arm could be used to close the jaws of the tool, while operator manipulation of the movable arm away from the fixed arm could open the jaws of the same tool. For tools that do not have an opening or closing action, operator manipulation of the movable arm in one direction could cause a first type of therapeutic or investigative effect/function, with operator manipulation of the movable arm in the opposite direction causing a second type of therapeutic or investigative effect/function, such as the alternate execution of cutting or coagulation actions by the same laser probe. It is also contemplated for the amount of movement of the movable arm in either direction away from its initial centrally-located neutral position to correlate to the amount of therapeutic or investigative effect/function achieved. Thus, springs are preferably used to create a biasing effect that permits an operator to sense an increase in resistance as operator-regulated force is increasingly applied, to naturally mimic the resistance that would otherwise be felt during direct manual manipulation of tissue by the tool's operative tip. The biasing springs also make the operator use more force to get the movable arm closer to a position of near maximum displacement (indicated by a plus sign), which results in the creation of more closure force between the blades at the tip of the interchangeable tool, as well as sufficient stored energy to bring the movable arm back into its initial neutral position (as the operator-applied force causing the out-of-neutral positioning lessens or is completely released). Further, even though each present invention instrument would be durably constructed and sufficiently strong for intended applications, a very small diameter telescopic port is used in the micro opening through the cavity wall, which provides the small diameter elongated rod with added support during its use especially in its lateral movement (side to side movement) in which the rod experiences the highest level of stress to its material (which allows the use of a smaller rod diameter). The telescopic port also allows for rotational movement of the rod, in addition to in and out movement that could be helpful during tool mounting onto the distal end of the elongated rod and during the use of the instrument inside the cavity. After tool mounting, the tool introducer is removed from the cavity where it remains available for bringing more tools into the cavity for mounting on different elongated rods, or entry into the cavity to remove a tool no longer needed and extract it. The tool introducer can also be used to mount multiple tools in succession on the same elongated rod to reduce the number of incisions made in a patient, or otherwise when appropriate to an application need. The small diameter electrical wiring or cable used to connect a mounted tool to its source of operative power remains extending through the regular-size port opening after tool introducer is withdrawn, and it leaves the cavity only when the attached probe or therapeutic device is extracted from the cavity upon the tool introducer. As an alternative to the use of electrical wiring or cable, it is also contemplated for the elongated rod to be adapted to transmit electricity through its core to a mounted tool (thus eliminating the need for external wires or cables to be introduced through the regular-size port opening. In addition, for patient protection all materials used for the present invention instrument, telescopic port, tool introducer, wires, cables, and interchangeable tools should be able to withstand without premature deterioration the repeated sanitizing procedures required for body cavity insertions, and strong enough to withstand the applied forces and pressures without breaking or deforming. Each should also be insulated, where needed, to prevent transmission of unnecessary electricity or heat to the patient. Thus, an important surgical benefit of the present invention is the potential use of several surgical, investigative, and/or therapeutic tools simultaneously (each secured to the distal end of a different present invention minimally-invasive instrument), while employing a very small diameter opening in patient skin for each minimally-invasive instrument used and only one regular-size port opening (for use in extending an optical system and needed wiring/cable into a cavity during tool operation), which minimizes the total magnitude/extent of incision required in a patient, thereby expediting patient recovery with excellent cosmetic outcome.

The description herein provides preferred embodiments of the present invention, but should not be construed as limiting its scope. For example, variations in the length and thickness dimensions of the fixed and movable arms of the handle grip; the diameter dimensions of the springs used in association with the movable arm; the length dimension of the elongated rod; the type of connecting means used to mount an interchangeable tool on the distal end of the elongated rod; the type of locking means used to secure an interchangeable tool on the cradle during tool introduction into a cavity; the diameter dimension of the different portions of the telescopic port; the diameter dimension of the thin wiring or cable used between the generator and the solenoid on the interchangeable tool mounted on the distal end of the elongated rod; the configuration of the beveled portion of the tool introducer used to facilitate wiring/cable removal; the size, number, and spaced-apart positioning of the exterior channels used in a sheath; and the length dimension of the cradle, other than those shown and described herein, may be incorporated into the present invention. Thus the scope of the present invention should be determined by the appended claims and their legal equivalents, rather than being limited to the examples given.

BRIEF DESCRIPTION OF THE DRAWINGS

FIG. 1 is a side view of the most preferred embodiment of the present invention multipurpose and minimally invasive instrument having a handle grip with a fixed arm and a movable arm that can be manipulated by an operator to control a tool mounted on the distal end of an elongated rod connected to the fixed arm via manipulation of the amount and/or polarity of electricity produced by a generator (or other device configured to provide metered power to the tool) that is electrically connected between the movable arm and the tool as shown in FIGS. 12 and 13, with at least one biasing spring located on each side of the movable arm that returns it to the neutral position shown in FIG. 1 after an operator has applied force to the movable arm to cause it to move toward or away from the fixed arm.

FIG. 2 is an enlarged view of a portion of FIG. 1, showing the fixed arm, movable arm, biasing spring means, and threaded connector secured to the fixed arm that is used for attachment of a supportive entry port means around the elongated rod.

FIG. 4a is a side view of a first interchangeable tool usable with the most preferred embodiment of the present invention that shows it having an operative distal end configured as a clamp, a connective end in a position opposed to the distal end and through which electrical wiring or cable extends (for connection of the tool to a power source outside the cavity via a regular-size port opening), and a solenoid positioned between the two opposed ends.

FIG. 4b is a sectional view of the first interchangeable tool shown in FIG. 4a.

FIG. 5b is a sectional view of the second interchangeable tool shown in FIG. 5a.

FIG. 8a is a bottom view of the tool introducer in FIG. 6 showing the centrally-positioned endoscopic bore, beveled surface and connecting channel, manual control knob, axle configured for rotational movement of the manual control knob, and two square bores each revealing a pulley that is attached to the axle connected to the manual control knob for guiding the movement of a belt that changes the angled orientation of the cradle as needed during the mounting of a tool on the distal end of the elongated rod, and although not shown it should be mentioned that an air tight valve is preferably placed over the opening of the endoscopic bore that allows the insertion of an optical system (endoscope/camera) through the endoscopic bore for operator viewing into the cavity while preventing any gas used to inflate the cavity from escaping before, during, or after optical system insertion.

FIG. 8b is a side view of a preferred embodiment of an optical system (laparoscope) that can be inserted through the endoscopic bore shown in FIG. 8a and used with the present invention.

FIG. 9a is bottom perspective view of the tool introducer previously shown in FIGS. 6, 7, and 8a.

FIG. 9b is a top perspective view of the tool introducer previously shown in FIGS. 6, 7, 8a, and 9a.

FIG. 10 is a perspective view of the tool introducer previously shown in FIGS. 6, 9a, and 9b having an interchangeable tool secured to its cradle.

FIG. 11 is an enlarged view of the cradle in FIG. 10 holding an interchangeable tool, and the preferred locking means used to secure the tool to the cradle during tool introduction and extraction from the cavity.

FIG. 13 is a perspective view of the same arrangement in FIG. 12 with the tool introducer removed, the electrical connection between the generator and solenoid on the tool remaining intact, and the optical system still extending through the regular-size port in side-by-side relation to the electrical wiring/cable connection.

LIST OF COMPONENTS 1. fixed arm of the minimally invasive instrument [shown in FIGS. 1, 2, 12, and 13]

2. electrical wiring (extending between the generator box #49 and the movable arm #14 and the fixed arm #1 of the minimally invasive instrument) [shown in FIGS. 1, 2, 12, and 13]

3. first biasing spring in the minimally invasive instrument's handle (allows an operator to sense an increase in resistance with an increase in operator-applied force that mimics the resistance the operator would otherwise feel during direct manipulation of tissue by the interchangeable tool's operative tip. The first biasing spring also makes the operator use more force to place movable arm #14 closer to the plus sign 11 to obtain more closure force between the blades at the tip of the interchangeable tool #33, #35 or other, and further, the stored energy in the first biasing spring resulting from the deployment of movable arm #1 away from its neutral starting position biases the movable arm #14 back into its neutral starting position when the operator-applied force causing the out-of-neutral positioning is no longer present) [shown with numbering in FIGS. 1 and 2, and shown without numbering in FIGS. 12 and 13]

4. second biasing spring in the minimally invasive instrument's handle (allows an operator to sense an increase in resistance with an increase in operator-applied force in the opposite direction to the force applied to move first biasing spring #3 out of its neutral starting position that mimics the resistance the operator would otherwise feel during direct manipulation of tissue by the interchangeable tool's operative tip. The second biasing spring also makes the operator use more force to place movable arm #14 closer to the plus sign 4 to obtain more opening force between the blades at the tip of the interchangeable tool #33, #35 or other, and further, the stored energy in the first biasing spring resulting from the deployment of movable arm #1 away from its neutral starting position biases the movable arm #14 back into its neutral starting position when the operator-applied force causing the out-of-neutral positioning is no longer present) [shown with numbering in FIGS. 1 and 2, and shown without numbering in FIGS. 12 and 13]

Figure 12:
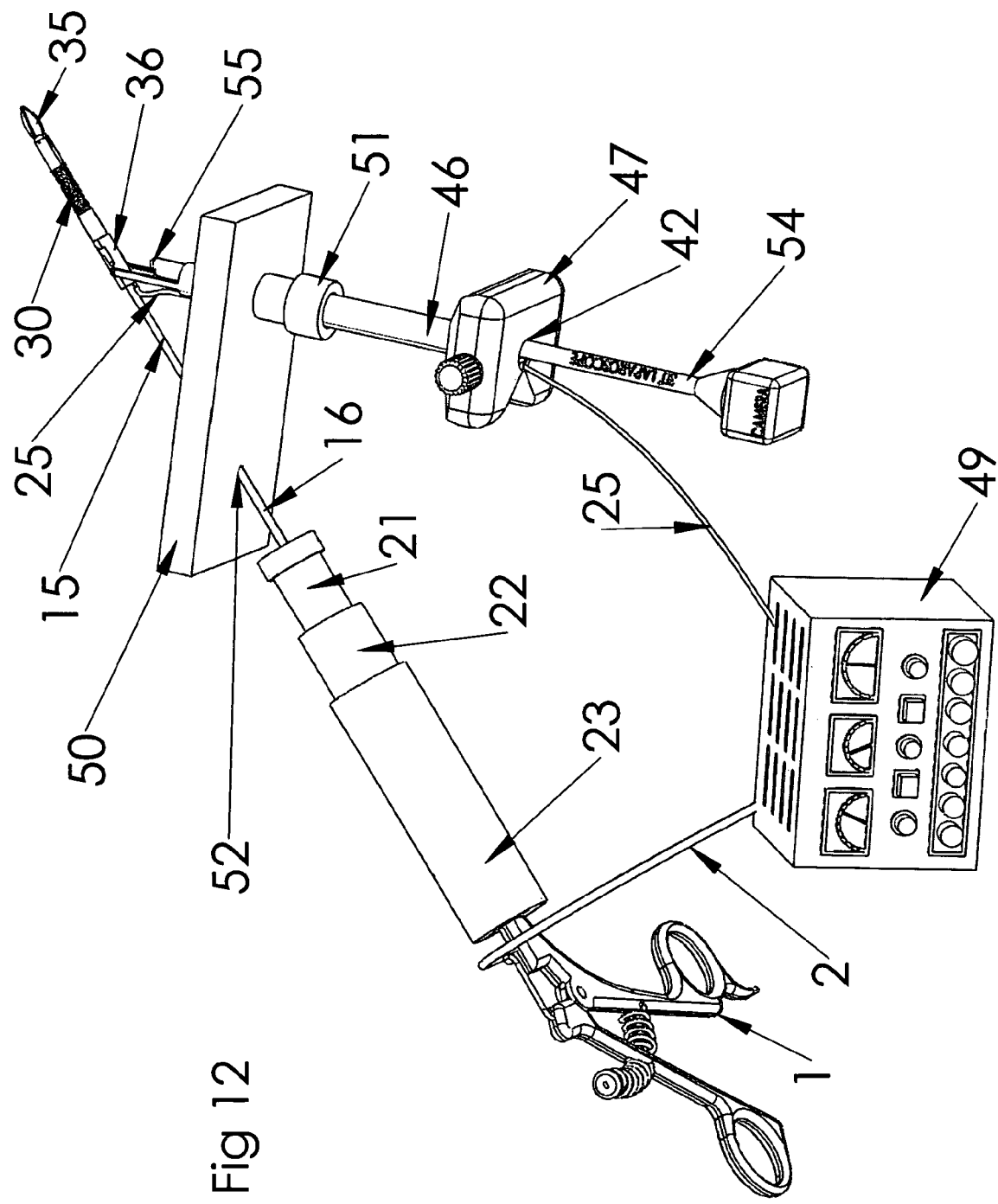
FIG. 12 is a perspective view of a cavity wall having a regular size opening (that represents the regular-size port) into which the tool introducer previously shown in FIGS. 6-8a and 9a-11 is inserted, an optical system inserted through the endoscopic bore in the tool introducer, the cavity wall also having a much smaller micro opening into which the telescopic port in FIGS. 4-5 is inserted, and further showing the elongated rod of the present invention instrument inserted through the narrow distal tube of the telescopic port, an interchangeable tool secured within the cradle of the tool introducer being attached to the distal end of the elongated rod, and a generator being electrically connected between the movable arm of the instrument's handle grip and the solenoid on the interchangeable tool.

5. pivoting connection between fixed arm #1 and movable arm #14 [shown with numbering in FIGS. 1 and 2, and shown without numbering in FIGS. 12 and 13]

6. telescopic port, with its narrow diameter distal tube #16 (that is inserted through a cavity wall #50 via a micro opening #52 and which increases support for elongated rod #15 during its use as a mount for an interchangeable tool #33, #35 or other) [shown in FIGS. 3a, 3b, 12, and 13]

7. finger and thumb engagement holes used for operator gripping of the minimally invasive instrument and movement of movable arm #14 toward and away from fixed arm #1 [shown with numbering in FIG. 2, and shown without numbering in FIGS. 12 and 13]

8. plus sign indicating direction of movement for movable arm #14 away from fixed arm #1 (from a centrally located neutral starting position) that may optionally reverse polarity (opposite polarity from that caused by movement of movable arm #14 between the minus sign #10 and plus sign #11) and provides an opening movement in a tool temporarily #33, #35 or other attached to the distal end/tip #13 of rod #15 (the closer the movable arm #14 gets to the plus sign #8, the stronger the force of opening between the tips of the blades on the interchangeable tool #33, #35 or other, or if the interchangeable tool does not have opening/closing action, as the movable arm #14 gets closer to the plus sign #8 the stronger the operative effect will be in the interchangeable tool, such as heat generation, laser function, and the like) [shown in FIG. 2]

9. minus sign indicating direction of movement for movable arm #14 toward fixed arm #1 (and back to the centrally located neutral position) that may optionally reverse polarity (opposite polarity from that caused by movement of movable arm #14 between the minus sign #10 and plus sign #11) and provides an opening movement in a tool temporarily attached to the distal end/tip #13 of rod #15 (the closer the movable arm #14 get to the minus sign #9 the weaker the force of opening between the tips of blades of the interchangeable tool #33, #35 or other, or if the interchangeable tool does not have opening/closing action, as the movable arm #14 gets closer to the minus sign #9 the weaker the operative effect will be in the interchangeable tool, such as heat generation, laser function, and the like) [shown in FIG. 2]

10. minus sign indicating direction of movement for movable arm #14 away from fixed arm #1 (and back to a centrally located neutral starting position) that may optionally reverse polarity (opposite polarity from that caused by movement of movable arm #14 between the minus sign #9 and plus sign # 8) and provides a closing movement in a tool temporarily attached to the distal end/tip #13 of rod #15 (the closer the movable arm #14 get to the minus sign #10 the weaker the force of closing between the tips of blades of the interchangeable tool #33, #35 or other, or if the interchangeable tool does not have opening/closing action, as the movable arm #14 gets closer to the minus sign #10 the weaker the operative effect will be in the interchangeable tool, such as heat generation, laser function, and the like) [shown in FIG. 2]

11. plus sign indicating direction of movement for movable arm #14 toward fixed arm #1 (from a centrally located neutral starting position) that may optionally reverse polarity (opposite polarity from that caused by movement of movable arm #14 between the minus sign #9 and plus sign # 8) and provides a closing movement in a tool temporarily attached to the distal end/tip #13 of rod #15 (the closer the movable arm #14 gets to the plus sign #11 the stronger the force of closing between the tips of blades of the interchangeable tool #33, #35 or other, or if the interchangeable tool does not have opening/closing action, as the movable arm #14 gets closer to the plus sign #11 the stronger the operative effect will be in the interchangeable tool, such as heat generation, laser function, and the like) [shown in FIG. 2]

12. connector attached to fixed arm #1 and having male threads for mating with the female threads #24 on the third telescoping tube #23 of telescopic port #6 [shown in FIGS. 1 and 2]

13. male-threaded distal end/tip of rod #15 configured for mating with the female threads #28 of the interchangeable tool #33 or #35 [shown in FIG. 1]

14. movable arm of the minimally invasive instrument [shown with numbering in FIGS. 1 and 2, and shown without numbering in FIGS. 12 and 13]

15. small diameter elongated rod connected to fixed arm #1 that extends beyond connector #12 [shown in FIGS. 1, 2, 12, and 13]

16. very small diameter tube with a sharp ends that extends from telescopic port 6 at one of its ends and which creates a micro opening #51 when it is inserted through a cavity wall #50 (the elongated rod #15 of the present invention instrument passes through tube #16 when it enters a cavity before an interchangeable tool #33, #35 or other is mounted on its distal end/tip #13 and when it exits a cavity after the mounted tool #33, #35 or other has been removed from distal end/tip #13) [shown in FIGS. 3a, 3b, 12, and 13]

17. sharp angled tip of tube #16 (it also can be tapered blunt tip conical shape to spread tissue open instead of cutting them to minimize trauma to the tissue) [shown in FIGS. 1 and 2]

Figure 3A:
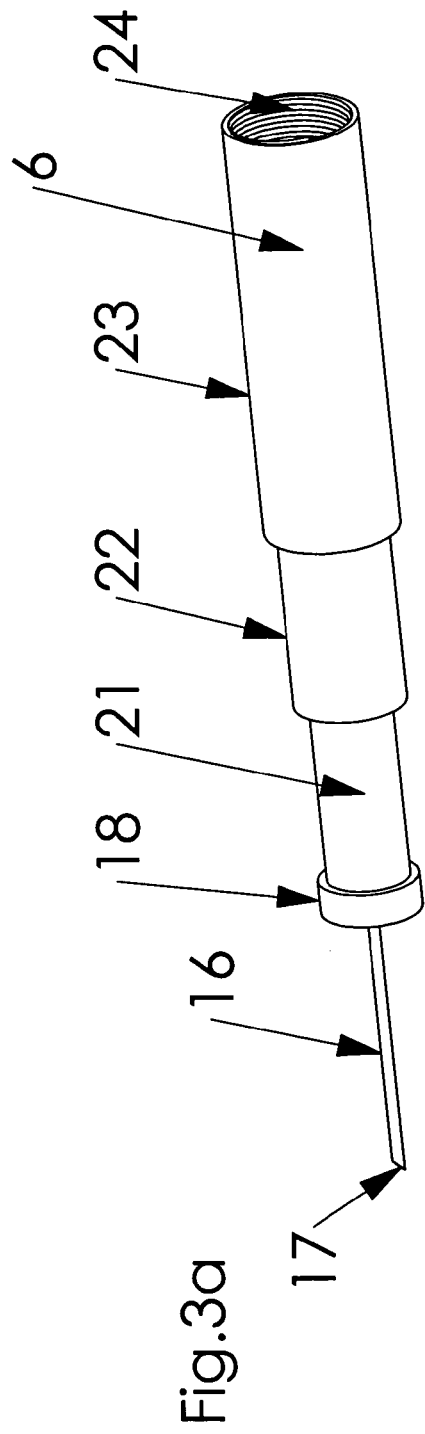
FIG. 3a is a side view of the most preferred embodiment of the telescoping supportive entry port means (also referred to as "telescopic port") that is attached to the threaded connector on the fixed arm of the handle grip, and is configured/dimensioned to support and protect the instrument's small diameter elongated rod during operation of a tool mounted on its distal end.
Figure 3B:
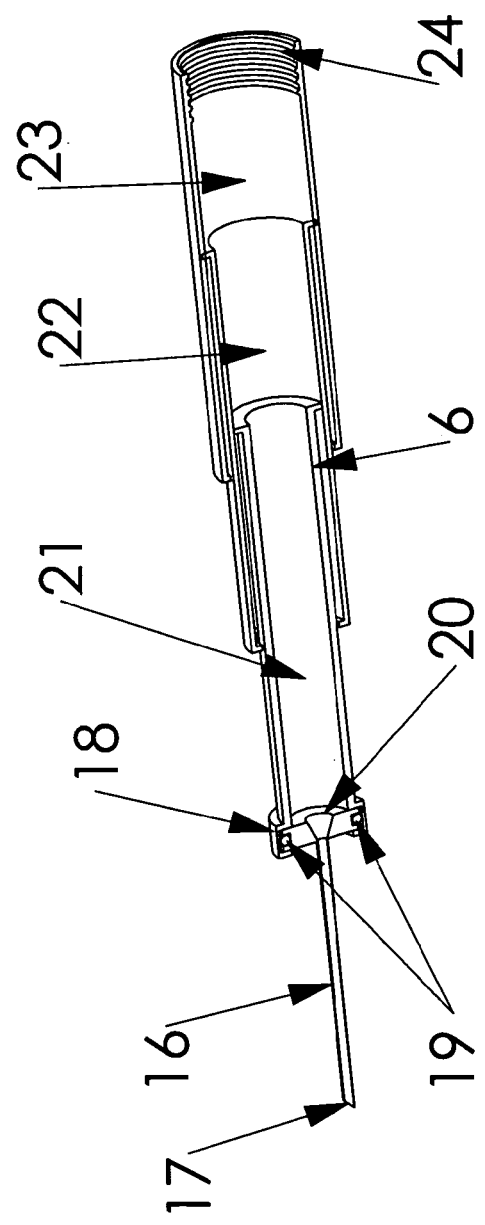
FIG. 3b is a sectional view of the telescopic port shown in FIG. 3a and having a threaded end in an opposed position to a very small diameter distal tube, with ball bearings located adjacent to the distal tube that permit rotational movement relative to the elongated rod.

18. stop ring for telescopic port #6 that houses the ball bearings #19 (that permit easy twisting of the minimally invasive instrument within the telescopic port #6 during the mounting of an interchangeable tool #33, #35 or other on the distal end/tip #13 of elongated rod #15 and during the use of the instrument in the cavity) [shown with numbering in FIGS. 3a and 3b, and shown without numbering in FIGS. 12 and 13]

19. ball bearings within stop ring #18 (that allow easy twisting of the minimally invasive instrument within the telescopic port #6) [shown in FIG. 3b]

20. central bore of tube #16 with cone-shaped proximal end (to allow easy insertion and passage of the elongated rod #15 through tube #16) [shown in FIG. 3b]

21. first telescoping tube of telescopic port #6 having the smallest diameter dimension [shown in FIGS. 3a, 3b, 12, and 13]

22. second telescoping tube of telescopic port #6 having a diameter dimension between that of first telescoping tube #21 and third telescoping tube #23 [shown in FIGS. 3a, 3b, 12, and 13]

23. third telescoping tube of telescopic port #6 having the largest diameter dimension [shown in FIGS. 3a, 3b, 12, and 13]

24. female threads on end of third telescoping tube #23 used for connection to male threads on the connector #12 attached to fixed arm #1 [shown in FIGS. 3a and 3b]

25. electrical wiring or cable used between control/generator box #49 and the linear solenoid #30 on interchangeable tool #33, #35 or other [shown in FIGS. 4a, 4b, 5a, 5b, 12, and 13]

Figure 5A:
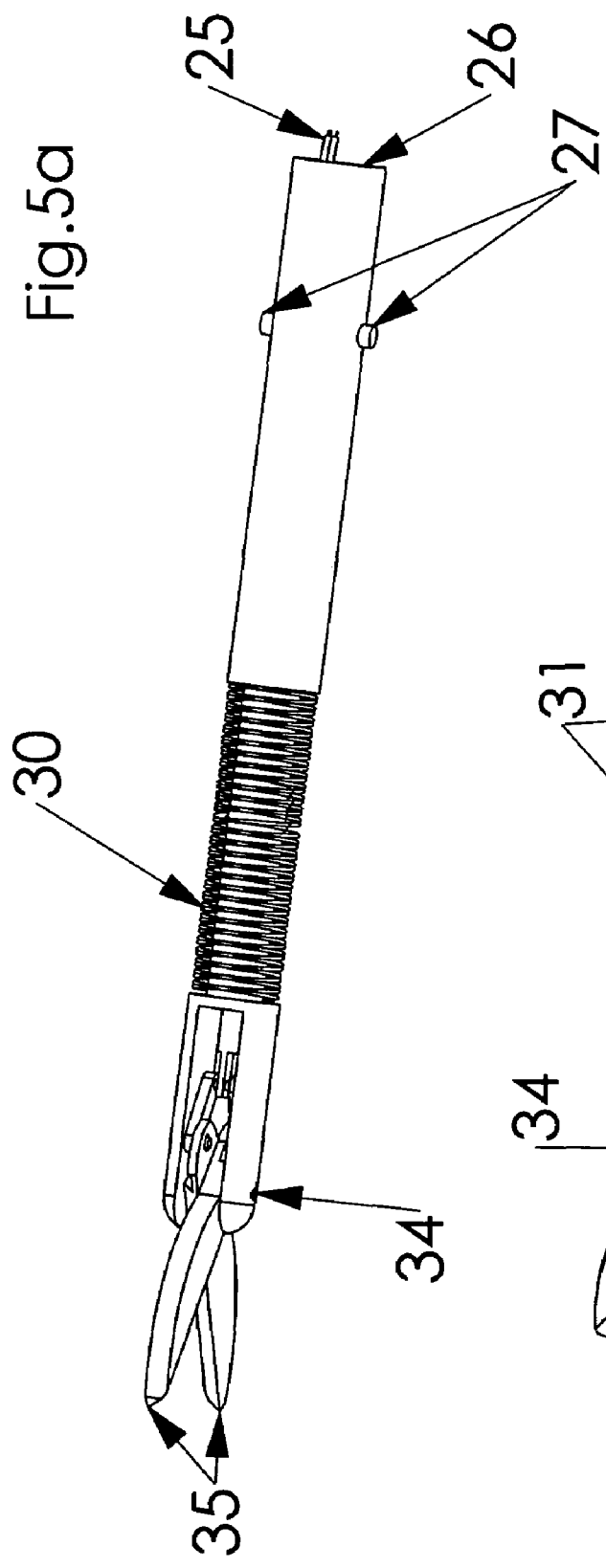
FIG. 5a is a side view of a second interchangeable tool usable with the most preferred embodiment of the present invention that shows it having an operative distal end configured as a cutting tool, a connective end in a position opposed to the distal end and through which electrically connective wiring or cable extends, and a solenoid between the two opposed ends.
Figure 5B:
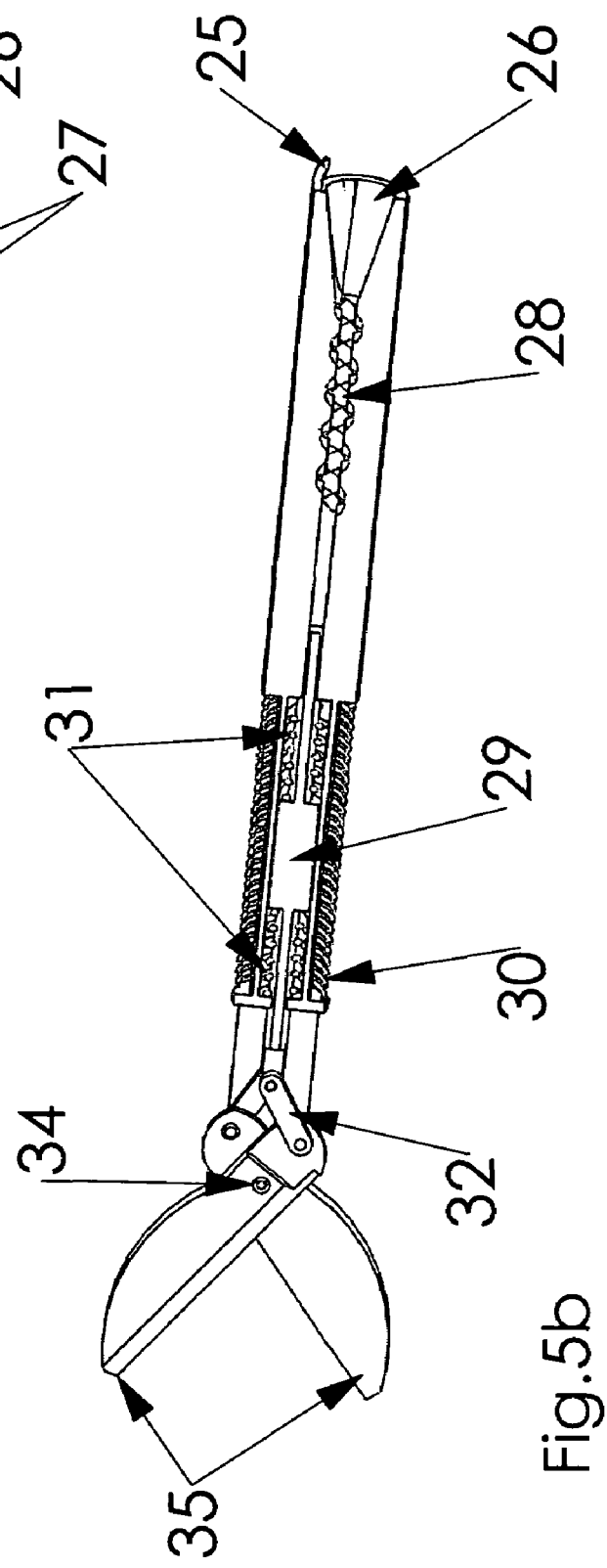

26. cone-shaped end of interchangeable tool #33, #35 or other that facilitates easy insertion and passage of the distal end/tip #13 of the elongated rod #15 for secure mounting of interchangeable tool #33, #35 or other upon elongated rod #15 [shown in FIGS. 4b and 5b]

27. opposed protrusions associated with the external surface of interchangeable tool #33, #35 or other (inserted into the locking configurations #37 on the cradle #36 of the tool introducer) [shown with numbering in FIGS. 4a, 5a, and 11, and without numbering in FIGS. 10 and 12]

28. female threading within interchangeable tool #33, #35 or other to hold the interchangeable tool #33, #35 or other onto the distal end/tip #13 of elongated rod #15 [shown in FIGS. 4b and 5b]

29. plunger (movable part of solenoid #30 that causes pivoting arms #32 to open and close) [shown in FIGS. 4b and 5b]

30. linear solenoid on the interchangeable tool #33, #35 or other (that causes the pivoting arms #32 of the interchangeable tool #33, #35 or other to open and close, thereby opening or closing the articulating members of a clamp or mechanical cutting tool or other mechanical tools, when it receives power from generator box #49 and controlled through the manual action of an operator's hand applying a force against movable arm #14 to cause it to move out of its neutral starting position) [shown with numbering in FIGS. 4a, 4b, 5a, 5b, 11, 12, and 13, and without numbering in FIG. 10]

31. internal springs (that return plunger #29 to a neutral starting position when movable arm #14 also returns to its neutral starting position) [shown in FIGS. 4b and 5b]
32. pivoting arms that in response to electrical activation of solenoid #30 mechanically open and close the operative end of an interchangeable tool (such as but not limited to the articulating members of clamping device #33 or mechanical cutting instrument #35) [shown with numbering in FIGS. 4b and 5b, and without numbering in FIGS. 4a, 5a, 10, and 11]
33. first interchangeable tool which is configured for attachment to the distal end/tip #13 of elongated rod #15 and has a clamping function [shown in FIGS. 4a and 4b]
34. pivot pin joining the articulating arms of clamping device #33 and mechanical cutting instrument #35 (that are opened and closed by movement of pivoting arms #32 in response to operator manipulation of movable arm #14 toward and away from fixed arm #1) [shown with numbering in FIGS. 4a, 4b, 5a, and 5b, and without numbering in FIGS. 10, 11, 12, and 13]
35. second interchangeable tool which is configured for attachment to the distal end/tip of elongated rod #15 and has a cutting function [shown with numbering in FIGS. 5a, 11, 12, and 13, and without numbering in FIG. 10]
36. pivoting cradle (configured to hold interchangeable tool #33, #35 or other during passage through a cavity wall #50 and can be made from transparent material) [shown with numbering in FIGS. 6, 7, 9a, 9b, 12, and 13, and without numbering in FIGS. 10 and 11]
37. U-shaped locking configuration (configured to mate with a protrusion #27 on interchangeable tool #33, #35, or other) [shown with numbering in FIGS. 6, 7, 9a, 9b, and 11, and without numbering in FIGS. 10 and 12]
38. opposed mounting arms associated with tool introducer/inserter #47 for pivoting attachment of cradle #36 [shown with numbering in FIGS. 6, 7, 9a, 9b, 10, and 11, and without numbering in FIG. 12]
39. belt for changing the angled orientation of cradle #36 relative to mounting arms #38 [shown in FIGS. 7, 10, and 11]
40. pulley attached to mounting arms #38 for guiding movement of belt #39 [shown with numbering in FIGS. 6, 7, 9b, and 10, and without numbering in FIG. 11]
41. channel in outside surface of tube #46 (for temporarily housing electrical wiring #25 during insertion of cradle #36 through regular-size port opening #51 in cavity wall #50) [shown with numbering in FIGS. 6, 7, 9a, 10, and 11, and without numbering in FIG. 8a]
42. interior bore longitudinally through shaft #46 (for insertion of an endoscopic camera or optical system so that it can be concurrently used while cradle #36 is employed to mount an interchangeable tool #33, #35 or other on the distal end/tip #13 of elongated rod #15) [shown with numbering in FIGS. 7, 8a, 9a, 9b, 11, and 12, and without numbering in FIG. 10]
43. manual control knob (has an axle for engaging pulley #45) [shown with numbering in FIGS. 6, 8a, 9a, 9b, and 10, and without numbering in FIG. 12]
44. square bore (for insertion of belt #39) [shown in FIGS. 8a and 9a]
45. pulley attached to the axle of manual control knob #43 (for guiding movement of belt #39 to change the angled orientation of cradle #36 during mounting and removal of interchangeable tool #33, #35 or other from elongated rod #15) [shown in FIG. 8a]
46. tubular shaft of tool introducer/inserter #47 [shown in FIGS. 6, 7, 9a, 9b, 10, 11, and 12]
47. tool introducer/inserter that transports an interchangeable tool #33, #35 or other through a regular-size port opening #51 in a cavity wall #50 for attachment to the elongated rod #15 of a present invention instrument (while allowing the concurrent use of an endoscopic camera or optical system in the same regular-size port opening #51). It has a wide bottom end that keeps the whole introducer from slipping through the endoscopic port into the cavity, stabilizes the introducer, and provides it with easy operator manipulation. [shown in FIGS. 6, 8a, 9a, 9b, 10, and 12]
48. beveled surface of the tool introducer/inserter #47 (allows for easy removal of electrical wiring #25 from channel #41 so that wiring #25 can remain extending through regular-size port opening #51 and provide power for operation of the interchangeable tool #33, #35 or other mounted on the distal end/tip #13 of elongated rod #15 after the shaft #46 of the tool introducer/inserter has been removed from regular-size port opening #51) [shown with numbering in FIGS. 6, 8a, 9a, 9b, and 10, and without numbering in FIG. 12]
49. control/generator box (provides electricity to linear solenoid #30 or any other function-generating device providing power to the interchangeable tools #33, #35, or other) [shown in FIGS. 12 and 13]
50. cavity wall [shown in FIGS. 12 and 13]
51. regular-size port opening (can possibly be as small as approximately five millimeters in diameter or have a greater diameter dimension, with the size being able to completely change depending on the application intended for the device, the materials used, and/or any other variables not accounted for here) [shown in FIGS. 12 and 13]
52. micro opening (can possibly be as large as approximately two millimeters in diameter dimension or less, with the size being able to completely change depending on the application the device is intended for, the materials used and or any other variables not accounted for here) [shown in FIGS. 12 and 13]
53. one of many possible additional control buttons (on the fixed arm of the minimally invasive instrument or elsewhere) that can be made to control extra functions in the interchangeable tools, such as but not limited to heat needed for cauterization, with size, configuration, spaced-apart positioning, and activation means (depressible, rocker, sliding, or other) being subjects of variation considered within the scope of the present invention. [shown in FIGS. 1 and 2]
54. optical system (camera system or endoscope, includes laparoscopes)—preferably an endoscope with a 30-degree angle tip [shown in FIGS. 8b and 12]
55. a 30-degree angle tip for optical system 54 [shown in FIGS. 8b and 12]
56. central opening through sheath 58, extends from one end of sheath 58 to the other (similar in function and configuration to the interior bore 42 longitudinally through shaft 46) [shown in FIGS. 14a and 14b]
57. channel formed in the exterior surface of sheath 58, not in communication with central opening 56, extends from one end of sheath 58 to the other, configured so that a wire or cable is easily contained within it and does not pop out prematurely before intentional release (one or more can be used on sheath 58) [shown in FIGS. 14a and 14b]
58. sheath with an enlarged diameter dimension on one of its ends to prevent its complete passage through the regular-sized port with which it is used (preferably having one central opening 56 and a plurality of channels 57 formed into its external surface) [shown in FIGS. 14a, 14b, and 14c]

DETAILED DESCRIPTION OF THE INVENTION

Although the present invention is not limited to surgical applications, and can be also used for therapeutic, investigative, and/or non-medical purposes, much of the discussion herein will be related to surgical applications and the benefits provided therein, such as when the elongated rod 15 of the present invention instrument is inserted into a body cavity using a micro opening 52 having a diameter dimension of approximately two millimeters or less (which it is capable of doing since it requires no internal space for the transport of wiring or cables 25 through a cavity wall 50 to use in operating a tool 33, 35, or other, mounted on its distal tip 13). The micro opening 52 used for insertion of the elongated rod 15 of a present invention device is typically no larger than that of a needle mark and capable of healing with little or no visible scar, thus reducing patient recovery time. Also, when several present invention devices are used to provide differing tools (33, 35, and others not shown) in the same cavity for surgical applications, each one is inserted through a similar micro opening 52 that leaves little or no visual scarring as a reminder of the procedure after it is complete. All other introduction of equipment across the cavity wall 50 is achieved via one regular-size port opening 51 (having a diameter dimension of approximately five millimeters or more and capable of leaving a small visible scar). It is through this regular-size port opening 51 that an endoscope/camera (shown in FIGS. 8*b*, 12, and 13 as part of the optical system identified by the number 54) is inserted to enable sufficient vision/viewing for the operator to guide the insertion and mounting of interchangeable tools (33, 35, and others) onto the distal tip 13 of elongated rod 15, as well as guiding the elongated rod 15 and its associated tool (33, 35, or other) to accomplish specific functions. As a result, during use of the present invention, all tools (33, 35, and others), optical systems 54 (camera/endoscope), electrical wiring or cable 25, and tool introducer 47 have access to a cavity through one regular-size port opening 51 that is expected to leave a scar, and repeated access through the single regular-size port opening 51 contributes no further trauma to a patient, whereas all of the present invention devices used in a cavity (perhaps two or three, or even more) to support a tool (33, 35, or other) during its use, each has its own elongated rod 15 that is independently inserted through cavity wall 50 via a separate micro opening 52, and each of these micro openings 52 is expected to be no larger than a needle mark and capable of healing with little or no visible scar. Therefore, instead of a patient being left with a large scar, or a visible scar for each piece of equipment used in surgical procedure, use of the present invention requires only one opening in a patient that is expected to leave a scar, which reduces patient recovery and improves cosmetic outcome, leading to enhanced patient satisfaction. It should be mentioned that although not shown, an air tight valve is preferably placed over the opening of the endoscopic bore 42 in tool introducer 47, and the central opening 56 in sheath 58, that allow the insertion of an optical system 54 (endoscope/camera) for operator viewing into the cavity while preventing any gas used to inflate the cavity from escaping before, during, or after optical system 54 insertion. A similar one-way valve could be associated with the opening in the angled tip 17 of very small diameter tube 16.

Figure 14A:
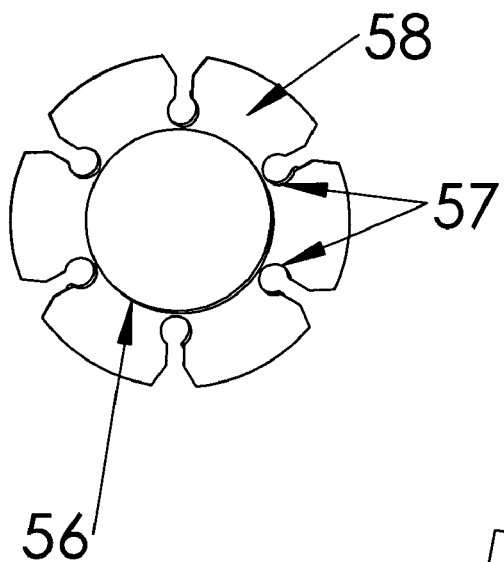
FIG. 14a is a front view of one end of a sheath that is used through the regular-size port opening in a cavity wall and showing its central opening used for insertion of an optical system (such as an endoscope or camera), and a plurality of channels positioned laterally to the central opening, but not in communication with it, that are used for separation of the different electrical wires or cables extending between the control/generator box and the linear solenoids on different interchangeable tools (attached to differing present invention devices) to keep the wires and cables from becoming entangled with one another.
Figure 14B:
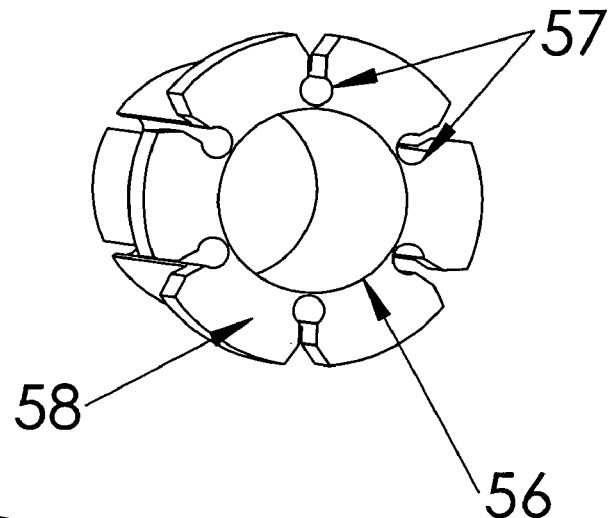
FIG. 14b is a perspective view of a sheath that can be used through the regular-size port opening in a cavity wall, with FIG. 14b showing the central opening used for insertion of an endoscope (optical system), a plurality of channels not in communication with the central opening that are used for separation of the different electrical wires or cables used between the control/generator box and the linear solenoids on different interchangeable tools to keep them from becoming entangled with one another, and the central opening and channels all extending the full length of the sheath.
Figure 14C:
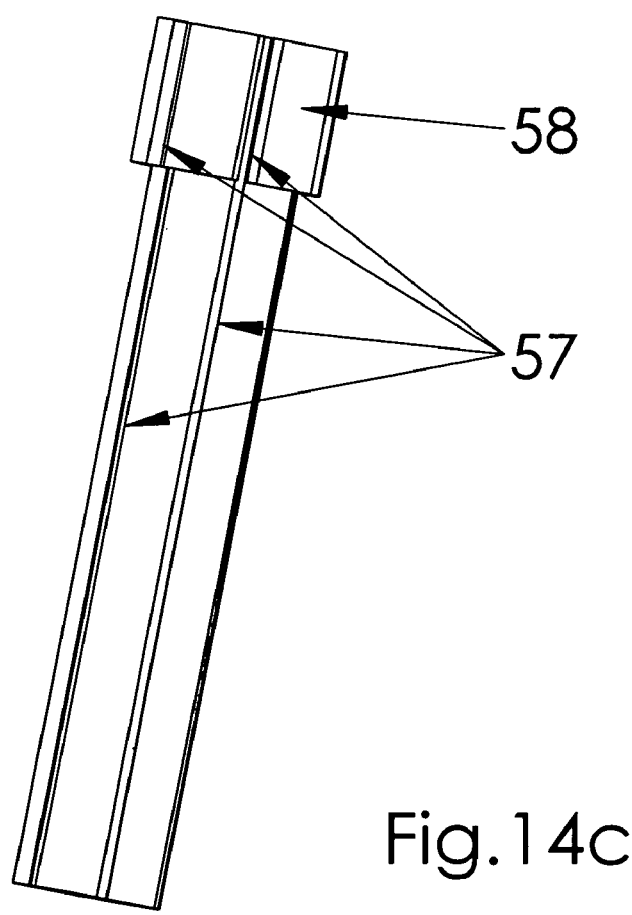
FIG. 14c is a side view of a sheath in FIGS. 14a and 14b showing several channels extending the full length of the sheath and the enlarged diameter dimension on one of its ends that prevents the entire sheath from entering through a cavity wall.

FIGS. 1 and 2 show the most preferred embodiment of the present invention multipurpose and minimally invasive instrument having a handle grip with a fixed arm 1 and a movable arm 14, at least two biasing springs 3 and 4 (one located on each side of movable arm 14), and an elongated rod 15 with a distal end/tip 13 upon which interchangeable tools 33, 35, and others (not shown) can be mounted. In contrast, FIGS. 3*a* and 3*b* show the most preferred embodiment of a telescopic port 6 (also referred to herein as "supportive entry port means") used with the multipurpose and minimally invasive instrument in FIGS. 1 and 2, with telescopic port 6 being configured and dimensioned to support and protect the instrument's small diameter elongated rod 15 during its use. FIGS. 4*a*, 4*b*, 5*a*, and 5*b* further show two interchangeable tools, respectively 33 and 35, usable with the most preferred embodiment of the present invention instrument, the tool 33 shown in FIGS. 4*a* and 4*b* having an operative distal end configured as a clamp, while the tool 35 shown in FIGS. 5*a* and 5*b* has an operative distal end configured as a cutting tool. With the exception of FIG. 8*b*, which shows a configuration of optical system 54, such as an endoscope or camera although not limited thereto, that can be used with the present invention instrument, FIGS. 6-8*a*, and 9*a*-11 show the most preferred embodiment of tool introducer 47 used to mount tools (33, 35 and other), one-at-a-time on the distal end/tip of elongated rod 15 of the present invention instrument after the tools used (33, 35 and other), have been inserted via tool introducer 47 through a cavity wall (shown in FIGS. 12 and 13 by the number 50). Tool introducer 47 is also used to withdraw tools (33, 35 and other) from the cavity after their use in the cavity is complete. The angle of the pivotally-mounted cradle 36 of tool introducer 47 is controlled from outside the cavity via a manual control 43 that is preferably positioned remotely from cradle 36 and near to the opposed end of tubular shaft 46. FIGS. 7, 8*a*, 9*a*, 9*b*, 10, and 11 also show a longitudinal bore 42 through tubular shaft 46 that is configured for the insertion of an endoscope/camera (shown in FIG. 8*b*, but also in FIGS. 12 and 13, as part of the optical system identified by the number 54, that also preferably has a thirty-degree angled tip 55 for off-axis viewing). It is important for tool inserter 47 and the optical system 54 (endoscope/camera) to be concurrently used in the same regular-size port opening 51 so that an additional port incision (not shown) does not have to be made in a patient to accommodate needed optical system 54 (endoscope/camera) use, and the use of longitudinal bore 42 makes this possible. FIGS. 12 and 13 show the most preferred embodiment of the present invention instrument in use with the telescopic port 6 and a power generator 49, as well as an optical system 54 and electrical wiring or cable 25 extending through the regular-size port opening 51 in cavity wall 50, with FIG. 12 also showing the shaft 46 of tool introducer 47 extending through the same regular-size port opening 51 in cavity wall 50, such that the optical system 54 is inserted through longitudinal bore 42. FIGS. 14*a-c* show varying views of a sheath 58 that can be used with a regular-size port opening 51 for preventing the entanglement of wires or cables 25 leading to multiple tools (33, 35, or other) located within a cavity as these tools are being used inside the cavity and after the tool introducer 47 has been removed from the regular-size port opening 51. For simplicity of identification and without any intent of limitation, the ensuing description will mainly focus on the interchangeable tool 33 and 35 shown, even though a wide variety of other interchangeable tools such as but not limited to laser probes and other heat-generating probes, are also contemplated to be within the scope of the present invention. Also, although not shown, it is contemplated for all openings and bores through a cavity wall 50 (at least in medical applications) to have an associated tight closure means configured to prevent escape of the carbon dioxide (or any other gas) used to inflate the cavity and provide adequate working room for the operator of the present invention. Such a tight closure means would also be needed for the longitudinal bore 42 through tool introducer 47. Also, of the ensuing description, the tool 35 shown in FIGS. 12 and 13 may be used as an example, without any intent of limitation.

FIG. 1 is a side view of the most preferred embodiment of the present invention multipurpose and minimally invasive instrument having a handle grip with a fixed arm 1 and a movable arm 14 that can be moved by an operator (not shown) toward and away from fixed arm 1 to control a tool (such as the tool 35 shown in FIGS. 5a and 5b) mounted on the distal end 13 of an elongated rod 15 connected to the fixed arm 1. Elongated rod 15 must be made from very strong material to withstand the strongest forces anticipated in an application, and for surgical applications elongated rod 15 needs to be made from non-corroding material that can be repeatedly sterilized without premature deterioration. As an option, elongated rod 15 can be made from conductive material and configured to transmit electricity through its core to an electrically-operated tool mounted thereon. However, in most applications, it is contemplated for an electrically-operated tool 35 to be mounted on the distal end 13 of elongated rod 15, with the wiring or cables 25 providing needed electrical power extending into the cavity via a regular-size port opening independent from the very small micro opening used for insertion of elongated rod 15. Control of tool 35 so that it can accomplish its intended function is via manipulation of the amount and/or polarity of electricity produced by a generator or other device configured to provide metered power to tool 35. For illustrative purposes, but without any intent of limitation, the simple generator/control shown in FIGS. 12 and 13 and identified by the number 49 will be used in the ensuing description as an example of a tool power source. Generator/ control 49 is electrically connected between the fixed arm 1 and the tool 35, with the electrical wiring 2 shown in FIGS. 1 and 2 providing the connection between generator/control 49 and fixed arm 1. Electrical wiring 2 also is connected between generator/control 49 and movable arm 14, as shown in both FIGS. 1 and 2. The electrical wiring or cable 25 shown in FIGS. 12 and 13 provides the connection between generator/ control 49 and tool 35. FIGS. 1 and 2 also show at least two biasing springs 3 and 4 (one located each side of movable arm 14) that assists in returning movable arm 14 to the neutral starting position illustrated after an operator has decreased the force applied to move the movable arm 14 to move away from or toward fixed arm 1. FIG. 1 also shows a connector 12 positioned between fixed arm 1 and elongated rod 15 that is used to securely attach telescopic port 6 over elongated rod 15 to protect and support it during its use. Male threads on connector 12 are configured to mate with complementary female threads 24 formed within the largest diameter tube 23 of telescopic port 6. Although threaded attachment between connector 12 and telescopic port 6 is preferred, such attachment is not critical and variations from that shown in FIGS. 1 and 2 may be used. Similarly, the distal end/tip 13 of elongated rod 15 appears to have male threads for attachment to the female threading 28 shown in FIG. 5b connecting with the cone-shaped proximal end 26 of interchangeable tool 35. However, such attachment is not critical and variations different from that shown, such as but not limited to a snap-fit connection, may also be used. In addition, FIG. 1 shows movable arm 14 and fixed arm 1 each having a finger or thumb engagement hole 7 that is configured to provide an easy and secure operator grip of the present invention instrument during its use. Although engagement holes 7 of similar size are shown to be a part of fixed arm 1 and movable arm 14, engagement holes 7 of differing size from that shown (or even differing size from one another) can also be used. In addition, the perimeter configurations, number used, and positioning of engagement holes 7 are not critical and variations different from that shown may be used as long as operator comfort is not significantly diminished. Further, although the configuration and dimensions of the remaining portions of fixed arm 1 and movable arm 14 shown attached to engagement holes 7 in FIGS. 1 and 2 are preferred, such configurations are not critical and variations different from that shown may also be used as long as the pivoting connection 5 between fixed arm 1 and movable arm 14 is preserved when a scissors-like action or function is needed in the tool 35 mounted on the distal end/tip 13 of elongated rod 15, and also as long as operator comfort is not significantly diminished. In addition, FIG. 1 shows one of many possible additional control buttons 53 that can be used on fixed arm 1, or elsewhere, to control extra functions in the interchangeable tools used (33, 35, or other), such as but not limited to heat needed for cauterization. The size, configuration, spaced-apart positioning, and activation means (such as depressible, rocker, sliding, or other) are not limited to that shown in FIGS. 1 and 2, and other configurations are also considered to be within the scope of the present invention.

In addition, the two biasing springs 3 and 4 shown in FIGS. 1 and 2, one located on each side of movable arm 14, alternatively assist in returning movable arm 14 to the neutral starting position illustrated after an operator has decreased the previously-applied force that caused it to move away from or toward fixed arm 1. As shown in FIGS. 1 and 2, biasing spring 3 is located between movable arm 14 and fixed arm 1, while biasing spring 4 extends outwardly from the side of movable arm 14 that is remote from fixed arm 1. As also shown in FIGS. 1 and 2, an un-numbered arcuate projection of rigid construction is shown with one or its opposed ends secured centrally to fixed arm 1 and its other end extending outwardly beyond movable arm 14. The first portion of the un-numbered arcuate projection, which is positioned between fixed arm 1 and movable arm 14, acts as a deployment guide for biasing spring 3. In contrast, the second portion of the un-numbered arcuate projection that extends outwardly beyond movable arm 14 acts as a deployment guide for biasing spring 4. Although not shown in the accompanying illustrations, it is contemplated for an opening to be made through movable arm 14 that permits a portion of the un-numbered arcuate projection/guide in FIGS. 1 and 2 to pass through movable arm 14 when an operator applies a force that moves movable arm 14 out of its neutral starting position and father away from fixed arm 1, or closer to it. Thus, this un-numbered arcuate projection/guide can work as an electric current control resistor, where the resistance is at its highest when the movable arm 14 is in the central neutral position, as well as at the negative signs 9 and 10, which significantly decreases the amount of electrical current transmitted to the acting portion of the interchangeable tool (example the linear solenoid) without causing any movement or effect. In contrast, the resistance to the electrical current decreases gradually when movable arm 14 moves toward the plus signs 8 or 11 (keeping in mind that one plus sign may represent a first polarity with the other plus sign representing the opposite polarity) thus increasing the amount of current transmitted to the acting portion of the interchangeable tool (one example of which would be the linear solenoid 30 shown in FIGS. 4a, 4b, 5a, and 5b) and causing increase in its movement or effect. The direction of the movement of the plunger 29 in solenoid 30 depends on the direction and/or the polarity of the current, which is controlled by the direction in which the movable arm 14 moves from its neutral starting position, whether toward plus sign 8 or plus sign 11. The plus signs designated by the numbers 8 and 11 in FIG. 2 indicate positions where a strong operational response to operator-applied forces is created in tool 35, with the minus signs designated by the numbers 9 and 10 in FIG. 2 indicating positions where a weak operational response is created in tool 35. Further, operator movement of movable arm 14 in the direction of plus sign 8 (wherein biasing spring 4 becomes at least partially compressed) provides a functional response perhaps with opposite polarity to that created when operator movement of movable arm 14 in the direction of plus sign 11 (wherein biasing spring 3 becomes at least partially compressed). As mentioned above, movable arm 14 is initially placed into a neutral position, wherein operator manipulation of movable arm 14 can occur in two directions, toward fixed arm 1 to increase the amount of electricity transmitted to the tool and create or enhance a first operative effect/function, with operator manipulation of the movable arm 14 away from the fixed arm 1 also increasing the amount of electricity transmitted to the tool 33, perhaps with opposite polarity so as to create a second operative effect/function. Thus, for a tool 35 that opens and closes, operator manipulation of the movable arm 14 away from fixed arm 1 could be used to open the jaws 32 of the tool 35 while operator manipulation of movable arm 14 toward fixed arm 1 could close the jaws 32 of the same tool. It is also contemplated for the scope of the present invention to include the reverse situation where opposite movements of movable arm 14 occur. For tools that do not have the opening or closing action of tool 35, operator manipulation of movable arm 14 in one direction could cause a first type of therapeutic or investigative effect/function, with operator manipulation of movable arm 14 in the opposite direction causing a second type of therapeutic or investigative effect/function, such as the alternate execution of cutting or coagulation actions by the same laser probe. It is also contemplated for the amount of movement of the movable arm 14 in either direction away from its initial centrally-located neutral position to correlate to the amount of therapeutic or investigative effect achieved. Thus, springs 3 and 4 are preferably used to create a biasing effect that permits an operator to sense an increase in resistance as operator-regulated force is increasingly applied, to naturally mimic the resistance that would otherwise be felt during direct manual manipulation of tissue (not shown) by the tool's operative tip (33, 35 or other). The biasing springs 3 and 4 also make the operator use more force to get the movable arm 14 closer to a position of near maximum displacement (indicated by a plus sign 8 or 11), which results in the creation of more closure force (or more opening force depending which plus sign it is closer too) between the blades at the tip of the interchangeable tool, as well as sufficient stored energy to assist in bringing the movable arm 14 back into its neutral starting position (as operator-applied force is decreased). Although the handle grip shown in FIGS. 1 and 2 has a fixed arm 1 and a movable arm 14, and permanent attachment to elongated rod 15 is also shown that is suitable for electrically operated tools 33 and 35 (identified in FIGS. 4a, 4b, 5a, and 5b), the configuration shown therein is not suitable for all electrically operated tools considered to be within the scope of the present invention. Therefore, even though not shown in the accompanying illustrations, it is contemplated for the handle grip connected to elongated rod 15 to also have other configurations. Thus, the handle grip used as a part of the present invention might be detachable from elongated rod 15, so that a handle with a different configuration can be substituted. Other examples of alternative handle grips, although not limited thereto, include those that are more ergonomic, those that incorporate different and/or multiple activating means, those that create a non-perpendicular angle between it and elongated rod 15 where doing so is advantageous in an application, and those that comfortably fit in the user's hand according to personal preference.

FIGS. 3a and 3b show the most preferred embodiment of a telescopic port 6 used with the multipurpose and minimally invasive instrument shown in FIGS. 1 and 2, which supports and protects elongated rod 15 during its use. Elsewhere in this description telescopic port 6 may also be referred to simply as a supportive entry port means. Telescopic port 6 has a very small diameter tube 16 connected to one end of a telescoping structure comprising three interconnected tubes 21, 22, and 23. Interconnected tubes 21, 22, and 23, in combination with very small diameter tube 16, provide a supportive entry port means for elongated rod 15 from laterally applied forces that could otherwise bend or break elongated rod 15. As shown in FIGS. 12 and 13, when the very small diameter tube 16 extends through a micro opening 52 in a cavity wall 50, a major portion of the elongated rod 15 connected to fixed arm 1 is in a protected position within tube 16. Only the end portion of elongated rod 15 behind cavity wall 50 is exposed so that it can be used to provide a secure mount for an interchangeable tool (33, 35 or other). FIGS. 3a and 3b also show the distal end of very small diameter tube 16 having an angled tip 17 that can be used to create the micro opening 52 of approximately two millimeters or less in a patient's skin. An opening larger than approximately two millimeters is usually not needed, as the interchangeable tools 33, 35 or other, do not pass through cavity wall 50 via micro opening 52, but instead pass through cavity wall 50 via a regular-size port 51 that is approximately five millimeters in diameter dimension or greater while being supported by the cradle 36 of an introducer/inserter device 47 having a tubular shaft 46 with a longitudinal bore 42 that allows concurrent use of an optical system 54 (endoscope/camera) when tubular shaft 46 occupies regular-size port 51. As shown in FIGS. 3a and 3b, the first telescoping tube 21 of telescopic port 6 has the smallest diameter dimension and is positioned the closest to very small diameter tube 16. The third telescoping tube 23 of telescopic port 6 has the largest diameter dimension and is placed into a position remote from first telescoping tube 21. The second telescoping tube 22 of telescopic port 6 has a diameter dimension between that of first telescoping tube 21 and third telescoping tube 23 and is also connected between them. While the use of three telescoping tubes 21, 22, and 23 is sufficient for present invention purposes, the use of a different number of telescoping tubes is also considered to be within the scope of the present invention. FIGS. 3a and 3b further show the third telescoping tube 23 of telescopic port 6 having a female-threaded proximal end 24 for engagement with male threads on the connector 12 that is attached to fixed arm 1 (and shown in FIGS. 1 and 2). Once the connection of female-threaded proximal end 24 is made to the male threads on connector 12, the present invention instrument and telescopic port 6 move together. The use of threads on proximal end 24 is not critical as long as some means of securely attaching third telescoping tube 23 to connector 12 is present. In the alternative, a snap-fit or twist-and-lock type of connection could be used, although not limited thereto. In addition, FIGS. 3a and 3b show a stop ring 18 positioned between the very small diameter tube 16 and the first telescoping tube 21 of telescopic port 6, which as shown in FIG. 3b houses the ball bearings 19 that permit easy twisting of the minimally invasive instrument's elongated rod 15 within telescopic port 6 during the mounting of an interchangeable tool (33, 35 or other) on the distal end/tip 13 of elongated rod 15 or during use of a mounted tool (33, 35 or other) inside the cavity. Ball bearings 19 within stop ring 18 also facilitate the attachment of the female-threaded proximal end 24 to the male threads on connector 12, wherein the twisting movement needed can be accomplished without rotating the very small diameter tube 16 extending to the micro opening 52 in cavity wall 50, which in surgical applications would cause additional trauma to the skin surrounding micro opening 52. FIG. 3b further shows a cone-shaped proximal end 20 leading to the central bore of very small diameter tube 16, which acts as a guide for elongated rod 15 and assists in more direct insertion of the distal end/tip 13 of elongated rod 15 through the central bore of tube 16, thereby lessening the opportunity for placing excess pressure on elongated rod 15 should an operator have elongated rod 15 misaligned with the central bore of tube 16 and attempt to force the two together. The configuration of telescopic port 6 with its ball bearings 19 also allows easy and free twisting movement of the elongated rod 15, and hence the interchangeable tool 35 mounted on the distal end 13 of rod 15, during its use inside the cavity without causing a similar twisting movement of the very small diameter tube 16. Further, the three telescoping tubes 21, 22, and 23, in addition to providing part of the protective means for elongated rod 15, provide in-and-out movement for elongated rod 15, and hence the interchangeable tool (33, 35, or other) mounted on the distal end/tip 13 of elongated rod 15, during its use inside the cavity without causing a similar in-and-out movement of the very small diameter tube 16 (the other part of the protective means for elongated rod 15). In contrast, where there is lateral or side-to-side movement of the elongated rod 15, and hence the interchangeable tool (33, 35, or other) mounted on the distal end 13 of rod 15, the telescopic port 6 with its very small diameter tube 16 moves with elongated rod 15 as one unit to add more support to it, since lateral or side-to-side movement is the type of movement in which elongated rod 15 encounters the highest strain from cavity wall 50. Although it is typically contemplated for each elongated rod 15 used behind cavity wall 50 for support of an electrically operated tool (33, 35, or other) to extend through the central bore of a different and independently positioned very small diameter tube 16, and then after use, for elongated rod 15 and its associated tube 16 to be removed from cavity wall 50 together, or for elongated rod 15 to be removed first, with tube 16 being removed shortly thereafter. However, it is also considered to be within the scope of the present invention for a first elongated rod 15 to be used within any tube 16, and after the first elongated rod 15 is removed therefrom, for one or more additional elongated rods each with a different handle grip structure to be successively inserted one-at-a-time through the same tube 16 before its removal from cavity wall 50.

FIGS. 4a, 4b, 5a, and 5b reveal the most preferred structure of two interchangeable tools 33 and 35 contemplated for mounting on the distal end/tip 13 of elongated rod 15, after being inserted through a cavity wall 50 while supported upon the cradle 36 of an introducer/inserter device 47 (shown in FIGS. 6-11). FIGS. 4a and 4b show the most preferred embodiment of a first interchangeable tool 35 usable with the present invention instrument and having an operative distal end configured as a clamp, while FIGS. 5a and 5b show the most preferred embodiment of a second interchangeable tool 35 usable with the present invention instrument and having an operative distal end configured as a mechanical cutting tool. In addition, FIGS. 4a, 4b, 5a, and 5b all show the pivot pin 34 that joins the articulating arms of clamping device 33 and mechanical cutting instrument 35, which are each opened and closed by movement of connected pivoting arms 32. Once a tool 33 or 35 is mounted on elongated rod 15, it is operator manipulation of movable arm 14 toward and away from fixed arm 1 that activates pivoting arms 32 to open and close the articulating arms of clamping device 33, mechanical cutting instrument 35, or other interchangeable tool (not shown). On the opposed connective end of each interchangeable tool 33 and 35, FIGS. 4a, 4b, 5a, and 5b show a cone-shaped configuration 26 that facilitates alignment and insertion of the male-threaded distal end/tip 13 of elongated rod 15 centrally within interchangeable tool (33, 35, or other) for mating with the female threads 28 shown in FIGS. 4b and 5b. In addition, FIGS. 4a, 4b, 5a, and 5b show electrical wiring or cable 25 extending from the connective end of interchangeable tools 33 and 35, which is connected between control/generator box 49 and the linear solenoid 30 on interchangeable tool (33, 35 or other) to provide power to solenoid 30 so that it can activate interchangeable tool (33, or 35 or other) to perform its operative function. FIGS. 4a, 4b, 5a, and 5b further show a linear solenoid 30 positioned on the interchangeable tools 33 and 35 close to its operative distal end. As shown by FIGS. 4b and 5b, linear solenoid 30 has a movable plunger 29 that deploys in response to power supplied by electrical wiring or cable 25 to cause pivoting arms 32 to open and close. As previously mentioned, the opening and closing of pivoting arms 32 cause the interchangeable tool (33, or 35 or other) to perform its operative function, whether mechanical or other. The internal springs 31 shown within solenoid 30 in FIGS. 4b and 5b return plunger 29 to a neutral starting position when movable arm 14 (of the handle grip shown in FIGS. 1 and 2) also returns to its neutral starting position, since power is no longer transmitted via electrical wiring or cable 25 from generator/controller 49 to solenoid 30. In addition, FIGS. 4a and 5a show opposed protrusions 27 that become inserted into the locking configurations 37 on cradle 36 (see FIG. 11) when the interchangeable tool (33, 35 or other) is carried by the cradle 36 of a tool introducer 47 through a cavity wall 50. The configurations of solenoid 30, pivoting arms 32, female threading 28, cone-shaped end 26, and protrusions 27 shown in FIGS. 4a, 4b, 5a, and 5b are merely representative thereof and should not be considered critical or limiting.

Figure 6:
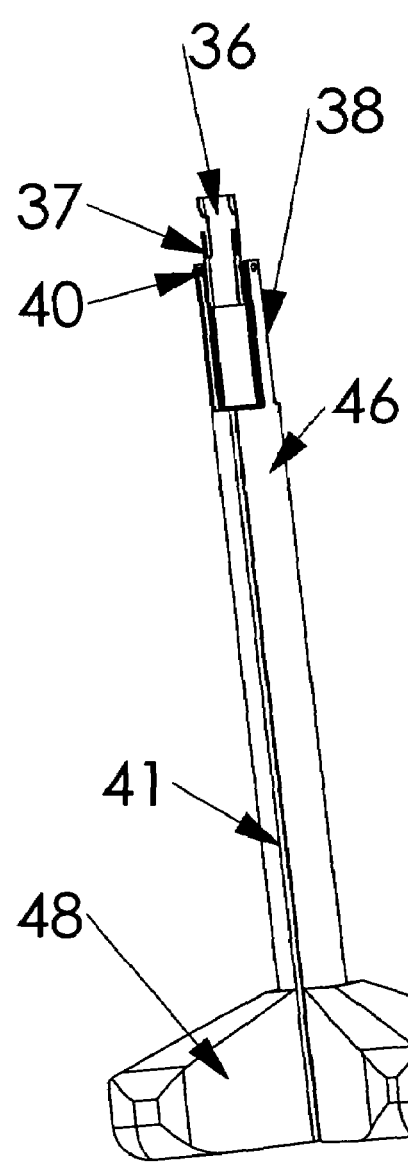
FIG. 6 is a perspective view of the tool introducer used with the most preferred embodiment of the present invention instrument and having a tubular shaft with a distal end, a cradle pivotally secured to mounting arms extending beyond the distal end and which is useable to introduce an interchangeable tool into a cavity and then mount it onto the distal end of the elongated rod (and also used to remove the tool from the rod and extract it from the cavity), a channel in the exterior/outside surface of the tubular shaft that extends into a beveled surface (used to facilitate wiring/cable removal), and a manual control in a position remote from the distal end that is used to pivot the cradle as needed during tool attachment to the elongated rod.
Figure 7:
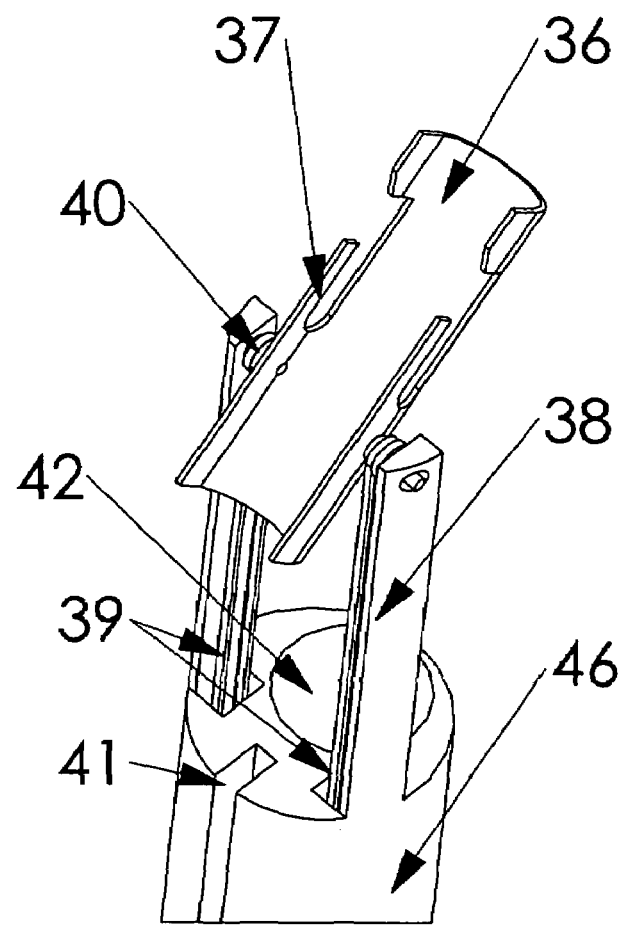
FIG. 7 is an enlarged view of the cradle and mounting arms shown in FIG. 6, that also shows an endoscopic bore extending the full length of the tubular shaft and more detail about the preferred locking means used to secure a tool to the cradle during tool introduction and extraction from the cavity.

FIGS. 6-11 show the most preferred embodiment of a tool introducer/inserter device 47 used to mount tools (33, 35 or other) one-at-a-time on the elongated rod 15 of the present invention instrument, after elongated rod 15 is inserted through a micro port 52 in a cavity wall 50, while each tool (33, 35 or other) enters the same cavity on the pivoting cradle 36 of the tool introducer 47 via a separate regular-size port 51. Tool introducer 47 is also used to withdraw tools (33, 35 or other) one-at-a-time from the cavity after their use in the cavity is complete. The angle of the pivotally mounted cradle 36 of tool introducer 47 is controlled via a manual control 43 that is remotely positioned from cradle 36 for operation outside the cavity. FIG. 6 provides a perspective view of the most preferred embodiment of tool introducer 47 used with the most preferred embodiment of the present invention instrument, while FIG. 7 provides an enlarged view of cradle 36, two mounting arms 38 for cradle 36 that upwardly depend beyond the upper edge of shaft 46, and the longitudinal bore 42 used for inserting the elongated part of an optical system 54 (endoscope/camera) so that the elongated part of the optical system 54 and tool introducer 47 can both be used simultaneously through regular-size port opening 51. Although not shown, for best visibility within a cavity, it is preferred for cradle 36 to be made from transparent materials, however, doing so is not critical. FIG. 8a provides a bottom view of tool introducer 47 showing the longitudinal bore 42 used for endoscope/camera insertion, beveled surface 48, and two square bores 44 each revealing a pulley 45 that is attached to the axle (not shown) connected to the manual control knob 43 and guides the movement of a belt that changes the angled orientation of the cradle 36 as needed during the mounting of a tool (33, 35, or other) on the instrument's elongated rod 15. In contrast, FIG. 8b shows a configuration of an optical system 54 in the form of a laparoscope and camera combination (also shown in FIGS. 12 and 13) that can be successfully inserted through longitudinal bore 42. FIGS. 9a and 9b respectively provide bottom and top views of tool introducer 47, while FIGS. 10 and 11 show tool introducer 47 with an interchangeable tool 35 mounted in cradle 36 and ready for insertion through regular-size port opening 51. It is preferred, but not critical, for locking configuration 37 of cradle 36 to be generally U-shaped, as shown in FIGS. 9a and 9b. As shown in the enlarged view of FIG. 7, cradle 36 is pivotally supported by opposed mounting arms 38 that extend beyond one end of shaft 46. Two belts 39 are shown in FIG. 7, each engaging a pulley 40 that guides the movement of its associated belt 39 for changing the angled orientation of cradle 36 relative to mounting arms 38 in response to operator manipulation of manual control 43. Although not limited thereto, an optical system 54 (such as an endoscope/camera system with an objective lens angle of approximately thirty to seventy degrees from horizontal) facilitates the monitoring needed when the interchangeable tool 35 in cradle 36 is mounted onto the distal end/tip 13 of elongated rod 15. An axle (shown in FIG. 8a, but not numbered) that is connected to manual control 43 is also associated with two pulleys 45 configured, dimensioned, and positioned for engaging belts 39. One pulley 45 is revealed in FIG. 8a through each of the square bores 44 adjacent to longitudinal bore 42. The enlarged view in FIG. 7 further shows tool introducer 47 having an interior longitudinal bore 42 that can be used to insert an optical system 54 (endoscope/camera), such as that shown in FIG. 8b, so that tool introducer 47 and the optical system 54 (endoscope/camera) can be used concurrently in the same regular-size port opening 51 in a cavity wall 50 and avoid making an extra patient incision. In addition, FIG. 7 shows a channel 41 in the outside surface of tubular shaft 46 that is used for temporarily housing (and protecting) electrical wiring or cable 25 connected to an interchangeable tool (33, 35, or other) while it is supported upon cradle 36 and during insertion of cradle 36 through a regular-size port opening 51 in a cavity wall 50. FIG. 6 shows channel 41 extending the full length of tubular shaft 46, so that as tool introducer 47 is withdrawn from a regular-size port opening 51 the electrical wiring or cable 25 is able to remain within the regular-size port opening 51 and provide the needed power to linear solenoid 30 to cause the interchangeable tool (33, 35 or other) mounted on elongated rod 15 to become activated so that it can fulfill its operative function. FIG. 6 also shows tool introducer/inserter 47 having a beveled surface 48 that allows for easy removal of electrical wiring or cable 25 from channel 41 so that wiring 25 can remain extending through the regular-size port opening 51 and provide power for operation of the interchangeable tool (33, 35 or other) mounted on the distal end/tip 13 of elongated rod 15, after the shaft 46 of the tool introducer/inserter 47 has been removed from regular-size port opening 51). Beveled surface 48 also allows for the use of a larger and more easily manipulated base for enhanced operator convenience. FIGS. 10 and 11 show tool introducer/inserter 47 having a tubular shaft 46 with a distal end and cradle 36 pivotally secured to the mounting arms 38 extending beyond the distal end that are useable to introduce an interchangeable tool (33, 35, or other) into a cavity and mount it onto the instrument's elongated rod 15.

FIG. 12 shows the most preferred embodiment of the present invention instrument in use with telescopic port 6, tool introducer 47, generator/control 49, electrical wiring 2, an optical system 54 with a thirty-degree angled tip 55 and the words "laparoscope" and "camera" marked thereon, and electrical wires or cable 25, while FIG. 13 shows tool introducer 47 removed and the electrical wiring or cable 25 connected between the generator/controller 49 and the linear solenoid 30 remaining within regular-size port opening 51 adjacent to optical system 54, which can comprise any camera, endoscope, laparoscope, or other optical system commonly used in minimally-invasive surgical procedures. FIG. 12 is a perspective view of a cavity wall 50 having a regular-size port opening 51 into which a tool introducer 47 is inserted, the cavity wall 50 also having a micro opening 52 into which the telescopic port 6 is inserted. The elongated rod 15 of the present invention instrument is inserted through the very small dimension tube 16 of the telescopic port 6, while an interchangeable tool 35 that is secured within the cradle 36 of the tool introducer 47 becomes attached to the distal end/tip 13 of elongated rod 15. The generator/controller 49 shown in FIGS. 12 and 13 is electrically connected via wiring to the movable arm 14 of the instrument's handle and via electrical wiring or cable 25 to the linear solenoid 30 on the interchangeable tool. To use the present invention, regular-size port opening 51 and micro opening 52 would first have to be established through cavity wall 50. However, since the bore 42 centrally through the longitudinal axis of tool introducer 47 can accommodate the insertion of an optical system 54 (such as but not limited to the endoscope or camera shown in FIG. 8b), one or more additional regular-size port openings 51 through cavity wall 50 to accommodate an optical system 54 are not needed, reducing patient trauma and improving cosmetic outcome. The angled tip 17 of the very small diameter tube 16 of telescopic port 6 can be used to create the needed micro opening 52. Thereafter, once the very small diameter tube 16 is in its usable position, the elongated rod 15 can be inserted through tube 16 and the female threads 24 on telescopic port 6 secured to the male threads on connector 12 attached to fixed arm 1 without disturbing patient tissue immediately around the micro port 51. Electrical connection of movable arm 14 and fixed arm 1 to generator/controller 49 can then be made via electrical wiring 2. Once an interchangeable tool 35 passes through the cavity wall 50 while mounted on the cradle 36 of a tool introducer 47, as shown in FIG. 12, an operator can manipulate manual control 43 to pivot cradle 36 so as to align interchangeable tool 35 with the distal end/tip 13 of elongated rod 15 and more easily secure interchangeable tool 35 to the distal end/tip 13 of elongated rod 15. The tool introducer 47 can then be withdrawn from regular-size port 51 and used to mount other interchangeable tools (33, 35 or other) to the elongated rods 15 of additional present invention instruments. Tool introducer 47 is also used to remove interchangeable tools (33, 35 or other) from elongated rod 15 and extract them via regular-size port opening 51 from the cavity wall 50. Either before or after tool introducer 47 transports an interchangeable tool (33, 35 or other) through regular-size port 51, electrical wiring or cable 25 can be connected between the linear solenoid 30 on interchangeable tool 35 and generator/controller 49. It must be understood that the illustration of generator/controller 49 is merely a representation thereof and may include variations not shown.

FIGS. 14a-c show a preferred embodiment of a sheath 58 that can be optionally used with the most preferred embodiment of the present invention. FIG. 14c shows the enlarged diameter dimension on one of the ends of sheath 58 that prevents it from completely entering a cavity through the regular-sized entry port 51 with which it is used. As shown in FIGS. 14a-c, sheath 58 preferably has one central opening 56 and a plurality of channels 57 formed into its external surface.

The central opening 56 through sheath 58 extends from one end of sheath 58 to the other, and has similar function and configuration to the interior bore 42 longitudinally through shaft 46. One or more channels 57 can be formed in the exterior surface of sheath 58. Channels 57 are not in communication with central opening 56, but do extend from one end of sheath 58 to the other, as does central opening 56. Channels 57 are also configured so that a wire or cable 25 is easily contained within it and does not pop out prematurely before intentional release by an operator. Sheath 58 is not used when the tubular shaft 46 of tool introducer/inserter 47 is inserted through regular-sized entry port 51, as shown in FIG. 12. Instead, as shown in FIG. 13, tool introducer/inserter 47 can be withdrawn from regular-sized entry port 51 (such as for the subsequent introduction of additional tools 33, 35, or other, one-at-a-time through regular-sized entry port 51). Sheath 58 is best used when all of the needed tools (33, 35, or other) have been inserted through regular-sized entry port 51 and are behind cavity wall 50 in positions ready for use. Although FIG. 13 does not show sheath 58, it is when the optical system 54 (endoscope/camera) and electrical wiring or cable 25 (one or many) have no other support, that sheath 58 can be effectively used to prevent wires or cables 25 from becoming entangled with one another and the optical system 54 (endoscope/camera) while its continued use enhances safety by permitting excellent operator viewing of all activity conducted within the cavity communicating with. In addition to the uses disclosed immediately above for sheath 58, and although not shown in the accompanying illustrations, it is also considered to be within the scope of the present invention for the central opening 56 of sheath 58 to be used for the introduction of a regular-size (larger than micro) surgical instrument, or other needed instrument, through regular-sized entry port 51 in place of optical system 54, but only after adequate optical viewing in the cavity accessed by regular-sized entry port 51 is already established via at least one prior-installed electrically operated imaging tool attached to the distal end/tip 13 of an elongated rod 15 positioned within the cavity. For safety and efficient function, it is critical that at least one electrically operated imaging tool is already attached to one of the elongated rods 15 extending through cavity wall 50, and that the operator confirms that each attached electrically operated imaging tool (camera, ultrasound, MRI or other) is properly functioning before beginning the temporary removal of main optical system 54 from the central opening 56 of sheath 58 that will make central opening 56 available for the introduction of a regular-size endoscopic instrument through cavity wall 50, or any other instrument needed to provide at least one function in the cavity that has a configuration sufficiently small to fit though central opening 56 in place of main optical system 54. Any electrically operated imaging tool (or tools) providing substitute viewing in the cavity after the main optical system 54 is temporary removed from central opening 56, would have to be inserted through regular-sized entry port 51 one-at-a-time via cradle 36 and introducer 47 (in the same manner as electrically operated tools 33 and 35 shown in FIGS. 4a, 4b, 5a, and 5b) with cradle 36 being pivoted to assist in the joining of the electrically operated imaging tool to the distal end/rip 13 of an associated elongated rod 15. Introduction and joining of each electrically operated imaging tool would be under the guidance of optical system 54 inserted through the interior bore 42 of introducer 47. Then, once proper operation is confirmed for all of the electrically operated imaging tools providing substitute viewing in the cavity while the main optical system 54 is absent, introducer 47 would be removed from the regular-sized entry port 51 with the main optical system 54 concurrently being removed, with sheath 58 subsequently being inserted through regular-sized entry port 51, where it would be available for the introduction of a regular-size surgical or other instrument through its central opening 56 under the guidance of the electrically operated imaging tool (or tools) previously joined to the distal end/tip of at least one elongated rod 15.

Thus, the present invention provides an instrument with a small diameter elongated rod 15 having a distal end/tip 13 that receives different interchangeable tools (33, 35, or other) one-at-a-time for a variety of surgical uses, including but not limited to surgery in abdominal and other body cavities, although other medical and non-medical applications involving search/rescue and scientific research are also contemplated. The number of present invention elongated rods 15 needed for use in a cavity depends upon the intended application, and each elongated rod 15 selected for support of an interchangeable tool (33, 35 or other) is separately inserted through the cavity wall 50 via a micro port 52 formed by the angled tip 17 of a supportive entry port means (also referred to herein for the most preferred embodiment of the present invention as telescopic port 6). In non-surgical applications, the opening used for inserting elongated rod 15 could be made by means other than angled tip 17. The supportive entry port means has two parts, a tube 16 having a very small diameter dimension extending from one end of the smallest of at least two tubes in telescopic relation to one another (tubes 21, 22, and 23 in FIGS. 3a and 3b), with the two parts associated with one another for allowing easy twisting and turning movement of said elongated rod without similar twisting and turning movement of very small diameter dimension tube 16, for allowing free movement of elongated rod 15 toward and away from a targeted working area within the space where it is used relative to the very small diameter dimension tube 16, but not the tubes in telescopic relation to one another, and also for supporting said elongated rod and moving with it as one unit when elongated rod 15 is subjected to laterally applied forces when moved laterally. Thus, when the distal end/tip 13 of elongated rod 15 is inserted through the hollow center of very small diameter tube 16, using its cone-shaped proximal end 20 as a guide, elongated rod 15 becomes supported and protected within very small diameter tube 16 and the remaining portions of the telescopic port 6 (such as the tubes 21, 22, and 23 in FIGS. 3a and 3b), with its distal end/tip 13 extending into the cavity and ready for receipt of an interchangeable tool (33, 35 or other). Mounting and removal of tools (33, 35 or other) from the distal end/tip 13 of elongated rod 15 are accomplished within the cavity. However, the micro bore 52 used for insertion of the distal tip/end 13 of the elongated rod 15 into the cavity is too small to use for introduction of interchangeable tools (33, or other) into the cavity, or withdrawal of interchangeable tools (33, 35 or other) from the cavity. Instead, needed insertion and withdrawal of interchangeable tools (33, 35 or other) from a cavity is accomplished by an independent tool introducer device 47 that passes through a regular-size port opening 51 in the cavity wall 50. Since reduced patient recovery time and improved cosmetic outcome are goals of present invention instrument use, a longitudinal bore 42 is formed through the shaft 46 of the tool introducer 47 to permit concurrent use of an optical system 54 (endoscope/camera), such as that shown in FIG. 8b, in the same regular-size port opening 51 occupied by the shaft 46 of the tool introducer 47, thereby precluding the need for an additional regular-size port opening 51 (approximately five millimeters in diameter or more) in a patient to separately introduce a camera and/or lighting into the cavity where an interchangeable tool (33, 35 or other) is mounted on the distal end/tip 13 of an elongated rod 15 and positioned for use. Thus, when needed for use in a limited access cavity, the elongated rod 15 of the present invention enters the cavity through the very small diameter tube 16 of a supportive entry port means (telescopic port 6), with both parts of telescopic port 6 (the very small diameter tube 16 and telescoping portions 21, 22, and 23) providing the small diameter elongated rod 15 with added support so that it can effectively function. Telescopic port 6 also allows for rotational movement helpful to its own attachment to the connector 12 secured to fixed arm 1, as well as transfer and attachment of electrically operated tools (33, 35 or other) from cradle 36 to the distal end 13 of the elongated rod 15. Interchangeable tools (33, 35 or other) needed for use in the cavity, including but not limited to imaging probes, surgical probes, sensor probes, clamping devices, cutting instruments, electromagnets, radio frequency probes, laser probes, laser cutting devices, laser coagulating instruments, heat-generating probes, image sensing probes, ultrasound probes, magnetic resonant imaging probes, and a variety of other devices, enter the cavity independently from the elongated rod 15 through a regular-size port opening 51 while being temporarily secured to the pivoting cradle 36 of the tool introducer 47, which is later removed from the regular-size port opening 51 once the tool becomes attached to the distal end 13 of elongated rod 15. Tool introducer 47 can be reinserted through regular size port 51 multiple times for the attachment (and removal) of a variety of electrically operated tools (33, 35 or other) to the same or different elongated rods 15 having distal end/tips 13 inserted within the same cavity. Once the tool introducer 47 is removed, the small diameter electrical wiring or cable 25 used to connect the mounted tool (33, 35 or other) to a source of operative power (such as but not limited to generator/controller 49) remains in an extended position through the regular-size port opening 51, which is also sufficiently large to receive an endoscope/camera (shown in FIG. 8*b* by the number 54) as well as the small diameter electrical wiring or cable 25 used to connect additional tools (33, 35 or other) that are mounted on the elongated rod 15 of several different present invention instruments to a source of operative power (such as but not limited to generator/controller 49), wherein the elongated rods 15 of any additional present invention instruments employed each enter the cavity through a separate and independent micro opening 52. Optionally a sheath 58 can be used to keep electrical wiring or cable 25 and the optical system 54 from becoming entangled during use and for easy removal from regular-size port opening 51 after use of an associated tool is complete. Although not limited thereto, it is contemplated that three or four present invention instruments will frequently be used at one time, and when this is done, sheath 58 expedites interchangeable tool removal and is very helpful to the operator. Further, as a result of the present invention using an elongated rod 15 to support a tool (instead of a tube as in prior art devices) and also using an external means of controlling tool (33, 35 or other) operation that is carried through the cavity wall 50 via an independent regular-size port opening 51, in contrast to the tubes used in prior art surgical, therapeutic, and investigative devices that contains interior means (wiring/cables) for tool operation control, the present invention can use micro openings 52 (having a possible maximum diameter dimension of approximately two millimeters but not limited thereto) that are not much bigger than a needle mark and able to heal with little or no visible scar. Thus, an important surgical benefit of the present invention is the potential use of several surgical, investigative, and/or therapeutic tools simultaneously (each secured to the distal end of a different present invention minimally-invasive instrument), while employing a micro opening 52 for each minimally-invasive instrument used and only one regular-size port opening 51 for most other cavity entry needs (such as concurrent use of an endoscope/camera and/or the electrical wiring or cable 25 connection between the linear solenoids 30 of each interchangeable tool used and a power source such as generator/controller 49), which expedites patient recovery with excellent cosmetic outcome.

The invention claimed is:

1. A multi-purpose minimally invasive instrument for medical, non-medical, surgical, therapeutic, and investigative applications in spaces and cavities having a wall blocking access thereto, and also having a larger entry port opening and at least one smaller entry port opening formed in the wall, said instrument comprising:

a handle;

an electrically operated tool that uses electrical power to perform at least one function, said electrically operated tool has a working end configured for performing said at least one function and an opposed connecting end;

a small diameter elongated rod having a first end in fixed association with said handle, and a second end configured for removable engagement with said connecting end of said electrically operated tool;

an optical system;

an introducer with a pivoting cradle configured for engaging and transporting said electrically operated tool through the larger entry port opening in the wall, said pivoting cradle also configured for easy release of said electrically operated tool once said connecting end of said operated tool becomes engaged with said second end of said elongated rod, said introducer further comprising a longitudinal bore configured and dimensioned to allow insertion of said optical system so that said introducer and said optical system can concurrently extend through the larger entry port opening in the wall, and said introducer also having a control knob configured to adjust the degree of tilting of said cradle for tool attachment from a location outside the space;

supportive entry port means for facilitating entry and exit of said elongated rod through the smaller entry port opening in the wall and support of said elongated rod during its use, said supportive entry port means also comprising a first part configured for extending through the smaller entry port opening in the wall and a second part configured for connection to said handle;

electrical transmission means adapted for connecting said handle and said electrically operated tool to a power source; and activation means adapted for initiating, controlling, and terminating performance of said at least one function of said electrically operated tool, said activation means also in electrical communication with said electrical transmission means, wherein when said introducer is inserted through the larger entry port opening in the wall visually guided by said optical system concurrently inserted with said introducer through the wall via positioning within said longitudinal bore of said introducer, and when said cradle of said introducer also engages and transports said electrically operated tool through the wall, and further when under guidance of said optical system said supportive entry port means transports said elongated rod through the smaller entry port opening in the wall so that said second end of said elongated rod extends beyond the wall and also beyond said supportive entry port means, under guidance of said optical system said control knob manipulates said cradle while said handle manipulates said elongated rod to join said second end of said elongated rod to said connecting end of said electrically operated tool and release said electrically operated tool from said cradle, after which removal of said introducer from the larger entry port opening in the wall with said optical system being concurrently removed, and reintroduction of said optical system through the larger entry port opening in the wall, allows said electrically operated tool via said electrical transmission means and said activation means to perform said at least one function under optical system guidance, and after said electrically operated tool has performed said at least one function, removal of said optical system from the larger entry port opening in the wall and re-insertion of said introducer through the larger entry port opening in the wall under guidance of said optical system housed within said longitudinal bore of said introducer, said control knob manipulates said cradle while said handle concurrently manipulates said elongated rod to remove said connecting end of said electrically operated tool from said second end of said elongated rod and transfer said electrically operated tool therefrom to said cradle, after which said introducer and said optical system are removed from the larger entry port opening in the wall while said electrically operated tool is secured to said cradle, whereafter if use of said elongated rod is complete, it also may be removed from the smaller entry port opening in the wall assisted by said supportive entry port means.

2. The instrument of claim 1 wherein said handle has a movable arm and a fixed arm, with said movable arm configured and positioned to start in a neutral position relative to said fixed arm so that said movable arm can move in two opposing directions, toward and away from said fixed arm to cause said electrically operated tool to perform a first function and a second function proportional to the amount movable arm deployment away from said neutral starting position; further comprising at least two biasing springs positioned and configured to allow an operator manipulating said handle to sense an increase in resistance with an increase in operator-applied force to said movable arm when the force applied moves said movable arm out of said neutral starting position and away from said fixed arm, and also to sense an increase in resistance with an increase in operator-applied force to said movable arm when the force applied moves said movable arm out of said neutral starting position in the opposite direction and toward said fixed arm, said biasing springs also configured to store potential energy when said movable arm is moved out of said neutral starting position that assists in returning said movable arm to said neutral starting position when the operator-applied force is decreased; and wherein said first end of said small diameter elongated rod is in fixed association with said fixed arm of said handle.

3. The instrument of claim 2 further comprising arcuate guide means for directing the movement of said biasing springs when said movable arm is not in said neutral starting position, with said arcuate guide means also configured for use in controlling the amount and polarity of the electrical current transmitted to said electrically operated tool.

4. The instrument of claim 1 wherein said first part of said supportive entry port means comprises a tube having a very small diameter dimension and said second part of said supportive entry port means comprises at least two tubes in telescopic relation to one another, said supportive entry port means also adapted for allowing easy twisting and turning movement of said elongated rod without similar twisting and turning movement of said first part, said supportive entry port means further adapted for allowing free movement of said elongated rod toward and away from a targeted working area within the space or cavity where it is used without similar movement of said first part, said supportive entry port means also adapted for supporting said elongated rod and moving with it as one unit when said elongated rod is moved laterally and subjected to laterally applied forces.

5. The instrument of claim 1 wherein said supportive entry port means further comprises structure selected from a group consisting of a stop ring with ball bearings engaged between said first part and said second part of said supportive entry port means and valves preventing escape of gas from a cavity.

6. The instrument of claim 1 wherein said electrically operated tool is selected from a group consisting of surgical probes, imaging probes, sensor probes, clamping devices, cutting instruments, laser cutting instruments, laser coagulating instruments, laser probes, electromagnets, heat-generating probes, image sensing probes, ultrasound probes, magnetic resonance imaging probes, and radio frequency probes.

7. The instrument of claim 1 wherein said electrically operated tool further comprises a linear solenoid configured for receiving electrical power from a power source via said electrical transmission mean and producing movement needed for said electrically operated tool to perform said at least one function after electrical power from the power source is received.

8. The instrument of claim 1 wherein said introducer further comprises at least one exterior channel configured and dimensioned for protecting the portion of said electrical transmission means providing electrical communication between a power source and said electrically operated tool.

9. The instrument of claim 8 wherein said introducer further comprises features selected from a group consisting of cradles comprising transparent material and beveled surfaces configured for facilitating removal of said electrical transmission means from said exterior channel.

10. The instrument of claim 1 further comprising a sheath configured for supporting an optical system and said electrical transmission means while they extend through the larger entry port opening formed in the wall after said electrically operated tool has been joined to said elongated rod and said introducer has been removed from the wall, said sheath having a central opening extending therethrough that is configured and dimensioned for insertion of an optical system, said sheath also comprising at least one longitudinally-extending external channel configured and dimensioned for protecting the portion of said electrical transmission means providing electrical communication between a power source and said electrically operated tool, said sheath further comprising opposing ends and an enlarged diameter dimension on one of said opposing ends that has sufficient size to prevent said sheath from moving completely through the larger entry port opening in the wall.

11. The instrument of claim 1 wherein said elongated rod comprises material configured for transmitting electricity to said electrically operated tool in a way that eliminates a need for external wiring.

12. A method of using the instrument of claim 1 for medical, non-medical, surgical, therapeutic, and investigative applications in spaces and cavities having a wall blocking access thereto, and also having a larger entry port opening and at least one smaller entry port opening formed in the wall, said method comprising the steps of:

(a) providing a power source, at least one or more electrically operated tool, and an optical system;

(b) using said electrical transmission means to connect said handle and a first said at least one electrically operated tool to a power source;

(c) connecting the first said at least one electrically operated tool to said cradle of said introducer;

(d) positioning said optical system within said longitudinal bore of said introducer;

(e) using said introducer to transport the first said at least one electrically operated tool and said optical system through the larger entry port opening in the wall while visually guided by said optical system, and also while said optical system is inserted through said longitudinal bore of said introducer;

(f) while visually guided by said optical system extending through the larger entry port opening that is positioned within said longitudinal bore of said introducer, positioning said supportive entry port means to provide an entry means for said elongated rod through the smaller entry port opening in the wall;

(g) connecting said second end of said supportive entry port means to said handle;

(h) while visually guided by said optical system, inserting said elongated rod through said supportive entry port means so that its second end extends beyond the wall and also beyond said supportive entry port means;

(i) joining said connecting end of the first said at least one electrically operated tool with said second end of said elongated rod under guidance of said optical system and by using said control knob to manipulate said cradle while at the same time using said handle to manipulate said elongated rod;

(j) also under guidance of said optical system and through use of said control knob and said handle, releasing the first said at least one electrically operated tool from said cradle;

(k) removing said introducer from the larger entry port opening in the wall with concurrent removal of said optical system;

(l) re-inserting said optical system through the larger entry port opening in the wall;

(m) using said handle, said electrical transmission means, and said activation means to cause the first said at least one electrically operated tool to perform said at least one function under guidance of said optical system inserted through the larger entry port opening;

(n) after the first said at least one electrically operated tool has performed said at least one function under optical system guidance provided via the larger entry port opening, removing said optical system from the larger entry port opening in the wall;

(o) inserting said introducer through the larger entry port opening in the wall while visually guided by said optical system, and also while said optical system is inserted through said longitudinal bore of said introducer;

(p) under optical system guidance using said control knob to manipulate said cradle while at the same time using said handle to manipulate said elongated rod to disengage the first said at least one electrically operated tools from said second end of said elongated rod and reestablish connection between the first said at least one electrically operated tool and said cradle;

(q) under optical system guidance provided via the larger entry port opening in the wall while said optical system is positioned within said longitudinal bore of said introducer, removing said elongated rod from said supportive entry port means;

(r) under optical system guidance removing said supportive entry port means from the smaller entry port opening in the wall such that in endoscopic applications a micro opening sufficiently small is left in a patient that allows for expedited patient recovery with excellent cosmetic outcome;

(s) under optical system guidance removing said introducer from the larger entry port opening in the wall with concurrent removal of the first said at least one electrically operated tool and said optical system; and (t) for each additional said at least one electrically operated tool provided and needed to perform a function while joined to said connective end of said one elongated rod after the first said at least one electrically operated tool, repeating in succession and under guidance of said optical system as needed said above steps (b) through (p) for the first said at least one electrically operated tool, until the last said at least one electrically operated tool has performed its function while joined to said connective end of said one elongated rod.

13. The method of claim 12 further comprising the steps of:

providing a plurality of elongated rods each in fixed association with a separate one of said handles and one said supportive entry port means for each of said elongated rods handles, and supportive entry port means, said elongate rods provided;

using said steps (f) through (h) above for each of said elongated rods and one of said supportive entry port means selected for association therewith to provide an entry means through the smaller entry port opening in the wall for said elongated rod, and also for connecting said selected and associated supportive entry port means to said handle fixed to said elongated rod, and further for positioning said elongated rod through said selected and associated supportive entry port means so that said second end of said elongated rod extends beyond the wall and also beyond said selected and associated supportive entry port means;

using said steps (b) through (g) above, and also said steps (i) through (m) above for connecting one of said electrically operated tools to said second end of each of said elongated rods extending beyond the wall;

using said steps (n) through (p) above to remove in succession all of said electrically operated tools previously connected to one of said elongated rods extending beyond the wall;

using said step (t) above for connecting and removing each additional one of said electrically operated tools needed for attachment in succession to any of said elongated rods; and removing each said elongated rod and each said supportive entry port means via steps (q) and (r) above.

14. The method of claim 13 wherein the order of said steps of using said electrical transmission means to connect said handle and a first one of said electrically operated tools to said power source, connecting said electrically operated tool to said cradle, and positioning said optical system within said longitudinal bore of said introducer is not critical, and further wherein the order of said step of connecting said second end of said supportive entry port means to said handle relative to said step of inserting said elongated rod through said supportive entry port means is also not critical, and in addition wherein when said elongated rod is made from electrically conductive material said step of connecting said electrically operated tool to said power source can occur after said step of joining said connecting end of said electrically operated tool with said second end of said elongated rod.

15. The method of claim 12 wherein said first part of said supportive entry port means comprises a tube having a very small diameter dimension and said second part of said supportive entry port means comprises at least two tubes in telescopic relation to one another, said supportive entry port means also adapted via a stop ring with ball bearings engaged between said first part and said second part for allowing easy twisting and turning movement of said elongated rod without similar twisting and turning movement of said first part, said supportive entry port means further adapted for allowing free movement of said elongated rod toward and away from a targeted working area within the space or cavity where it is used without similar movement of said first part, and said supportive entry port means also adapted for supporting said elongated rod and moving with it as one unit when said elongated rod is moved laterally and subjected to laterally applied forces.

16. The method of claim 12 wherein said handle has a movable arm and a fixed arm, with said movable arm configured and positioned to start in a neutral position relative to said fixed arm so that movement of said movable arm can be in two opposing directions, toward and away from said fixed arm; and further comprising the steps of providing at least two biasing springs and positioning said biasing springs to allow an operator manipulating said handle to sense an increase in resistance with an increase in operator-applied force to said movable arm when the force applied moves said movable arm out of said neutral starting position and away from said fixed arm, and also to sense an increase in resistance with an increase in operator-applied force to said movable arm when the force applied moves said movable arm out of said neutral starting position in the opposite direction and toward said fixed arm, and wherein said positioning of said biasing springs also allows said biasing springs to store potential energy when said movable arm is moved out of said neutral starting position that assists in returning said movable arm to said neutral starting position when the operator-applied force is decreased; and the steps of further providing arcuate guide means, positioning said arcuate guide means for directing movement of said biasing springs when said movable arm is not in said neutral starting position, and wherein said positioning of said arcuate guide means also allows control of the amount and polarity of the electrical current transmitted to said electrically operated tool, and further comprising the step of manipulating said handle to move said movable arm toward said fixed arm to cause said electrically operated tool to perform a first function with the intensity of said first function being proportional to the amount movable arm deployment away from said neutral starting position; and in addition comprising the step of manipulating said handle to move said movable arm away from said fixed arm to cause said electrically operated tool to perform a second function with the intensity of said second function being proportional to the amount movable arm deployment away from said neutral starting position in the opposite direction.

17. The method of claim 12 wherein said electrically operated tool further comprises a linear solenoid configured for receiving electrical power from a power source via said electrical transmission mean and producing movement needed for said electrically operated tool to perform said at least one function after electrical power from the power source is received.

18. The method of claim 12 wherein said introducer further comprises features selected from a group consisting of cradles comprising transparent material, exterior channels configured and dimensioned for protecting the portion of said electrical transmission means providing electrical communication between a power source and said electrically operated tool, and beveled surfaces configured for facilitating removal of said electrical transmission means from said exterior.

19. The method of claim 12 further comprising the step of providing a sheath configured for supporting said optical system and said electrical transmission means while they extend through the larger entry port opening formed in the wall after said electrically operated tool has been joined to said elongated rod and said introducer has been removed from the wall, said sheath having a central opening extending therethrough that is configured and dimensioned for insertion of an optical system, said sheath also comprising at least one longitudinally-extending external channel configured and dimensioned for protecting the portion of said electrical transmission means providing electrical communication between a power source and said electrically operated tool, said sheath further comprising opposing ends and an enlarged diameter dimension on one of said opposing ends that has sufficient size to prevent said sheath from moving completely through the larger entry port opening in the wall, and further comprising the step of inserting said sheath through the larger entry port opening in the wall when said introducer is not present therein and concurrently positioning said sheath relative to said optical system and said electrical transmission means so that said optical system extends through said central opening and said electrical transmission means extends through said at least one longitudinally-extending external channel, and entanglement of said electrical transmission means and said optical system is avoided.

20. The method of claim 12 wherein said elongated rod comprises material configured for transmitting electricity to said electrically operated tool in a way that eliminates a need for external wiring, and further comprising the step of connecting said electrically operated tool to said power source after said step of joining said connecting end of said electrically operated tool with said second end of said elongated rod.

* * * * *